US010621645B2

(12) United States Patent
Toupin

(10) Patent No.: US 10,621,645 B2
(45) Date of Patent: Apr. 14, 2020

(54) SYSTEM, METHOD, AND NON-TRANSITORY COMPUTER-READABLE STORAGE MEDIA FOR ENDLESS AISLE OF PRODUCTS IN RETAIL STORE

(71) Applicant: Wal-Mart Stores, Inc., Bentonville, AR (US)

(72) Inventor: Justin Toupin, San Francisco, CA (US)

(73) Assignee: WALMART APOLLO, LLC, Bentonville, AR (US)

( * ) Notice: Subject to any disclaimer, the term of this patent is extended or adjusted under 35 U.S.C. 154(b) by 532 days.

(21) Appl. No.: 15/009,598

(22) Filed: Jan. 28, 2016

(65) Prior Publication Data

US 2017/0221123 A1 Aug. 3, 2017

(51) Int. Cl.
*G06Q 30/00* (2012.01)
*G06Q 30/06* (2012.01)
*G16H 10/00* (2018.01)

(52) U.S. Cl.
CPC ..... *G06Q 30/0631* (2013.01); *G06Q 30/0625* (2013.01); *G16H 10/00* (2018.01)

(58) Field of Classification Search
CPC .................................. G06Q 30/0631
See application file for complete search history.

(56) References Cited

U.S. PATENT DOCUMENTS 6,543,683 B2    4/2003   Hoffman
6,711,460 B1    3/2004   Reese
(Continued)

FOREIGN PATENT DOCUMENTS

WO    2000075834 A2    12/2000
WO    2007134378 A1    11/2007
WO    2012064026 A2    5/2012

OTHER PUBLICATIONS

Sanjit Jung Thapa (Oct. 2015) eMedication—a smartphone-based e-medication system for hospitalized patients. pp. 1-76 The Arctic University of Norway faculty of science and technology. (Year:2015) (Year: 2015).*

(Continued)

*Primary Examiner* — Michael Misiaszek
*Assistant Examiner* — Jason B Warren
(74) *Attorney, Agent, or Firm* — Bryan Cave Leighton Paisner LLP

(57) ABSTRACT

A system, method, and non-transitory computer-readable storage media includes a computer system configured to receive a selected product to be located in a retail store of a retailer inputted by a user into a mobile computer application running on a mobile computing device, to perform a search for the selected product on a plurality of products records corresponding to a plurality of products offered by the retailer, to identify one or more of the product records relevant to the selected product, to transmit the one or more product records identified as one or more search results, to provide the one or more search results to the mobile computer application running on the mobile computing device, each of the one or more search results being associated with a product offered by the retailer, and to suggest at least one related product to the selected product, and to receive at least one product or at least one related product from the search results selected by the user using the mobile computer application running on the mobile computing device to be shipped to an address of the retail store or another address inputted by the user.

20 Claims, 20 Drawing Sheets

(56) References Cited

U.S. PATENT DOCUMENTS

| | | | |
|---|---|---|---|
| 6,898,598 B2 | 5/2005 | Himmel et al. | |
| 7,487,912 B2 | 2/2009 | Seifert et al. | |
| 8,606,698 B2 | 12/2013 | Schultz et al. | |
| 9,043,217 B2 | 5/2015 | Cashman et al. | |
| 9,195,959 B1* | 11/2015 | Lopez | G06Q 10/08 |
| 9,607,345 B1 | 3/2017 | Hendren et al. | |
| 2002/0073043 A1 | 6/2002 | Herman et al. | |
| 2003/0120607 A1 | 6/2003 | Piotrowski | |
| 2003/0216950 A1 | 11/2003 | Chen | |
| 2004/0204954 A1 | 10/2004 | Lacko | |
| 2004/0236635 A1 | 11/2004 | Publicover | |
| 2005/0165651 A1 | 7/2005 | Mohan | |
| 2007/0088624 A1 | 4/2007 | Vaughn et al. | |
| 2007/0124170 A1 | 5/2007 | Cabell et al. | |
| 2007/0150375 A1 | 6/2007 | Yang | |
| 2007/0204169 A1 | 8/2007 | Bahl et al. | |
| 2007/0226071 A1 | 9/2007 | Kern et al. | |
| 2009/0271265 A1 | 10/2009 | Lay et al. | |
| 2011/0016007 A1 | 1/2011 | Shiftan et al. | |
| 2011/0231272 A1 | 9/2011 | Englund et al. | |
| 2011/0307265 A1 | 12/2011 | Bannis | |
| 2012/0072311 A1 | 3/2012 | Khan | |
| 2012/0078673 A1 | 3/2012 | Koke et al. | |
| 2012/0084391 A1 | 4/2012 | Patel et al. | |
| 2012/0114116 A1 | 5/2012 | Sulaiman et al. | |
| 2012/0166298 A1 | 6/2012 | Smith et al. | |
| 2012/0191573 A1 | 7/2012 | Miller | |
| 2012/0221446 A1 | 8/2012 | Grigg et al. | |
| 2012/0290609 A1 | 11/2012 | Britt | |
| 2013/0173403 A1 | 7/2013 | Grigg et al. | |
| 2013/0179180 A1 | 7/2013 | Patra | |
| 2013/0196297 A1 | 8/2013 | Anwar | |
| 2013/0224694 A1 | 8/2013 | Moore et al. | |
| 2013/0290145 A1* | 10/2013 | Durst, Jr. | G06Q 30/0629 705/26.64 |
| 2014/0156297 A1 | 6/2014 | Schaefer et al. | |
| 2014/0188648 A1 | 7/2014 | Argue et al. | |
| 2014/0222482 A1 | 8/2014 | Gautam et al. | |
| 2014/0279269 A1 | 9/2014 | Brantley et al. | |
| 2015/0161353 A1* | 6/2015 | Emerson | G06F 19/3456 705/2 |
| 2015/0242592 A1 | 8/2015 | Weiss et al. | |
| 2015/0261934 A1 | 9/2015 | Miller | |
| 2015/0294084 A1 | 10/2015 | McCauley et al. | |
| 2015/0294387 A1* | 10/2015 | Karmazyn | G06Q 30/0623 705/26.61 |
| 2016/0132660 A1* | 5/2016 | Barajas | G06Q 10/10 705/2 |
| 2016/0364547 A1 | 12/2016 | Love | |
| 2017/0213271 A1 | 7/2017 | Nelms et al. | |
| 2017/0220649 A1 | 8/2017 | Toupin | |
| 2017/0220684 A1 | 8/2017 | Toupin et al. | |
| 2017/0220741 A1 | 8/2017 | Toupin et al. | |
| 2017/0220761 A1 | 8/2017 | Toupin et al. | |
| 2017/0220762 A1 | 8/2017 | Toupin et al. | |
| 2017/0220763 A1 | 8/2017 | Toupin et al. | |
| 2017/0220764 A1 | 8/2017 | Toupin et al. | |
| 2017/0220765 A1 | 8/2017 | Toupin et al. | |
| 2017/0220770 A1 | 8/2017 | Toupin et al. | |
| 2017/0220771 A1 | 8/2017 | Toupin et al. | |
| 2017/0221129 A1 | 8/2017 | Toupin | |

OTHER PUBLICATIONS

U.S. Appl. No. 15/009,327, filed Jan. 28, 2016 Entitled "System, Method, and Non-Transitory Computer-Readable Storage Media for Displaying Information on Mobile Devices".

U.S. Appl. No. 15/009,374, filed Jan. 28, 2016 Entitled "System, Method, and Non-Transitory Computer-Readable Storage Media for Evaluating Search Engine Results and Displaying a Virtual Pill Case".

U.S. Appl. No. 15/009,417, filed Jan. 28, 2016 Entitled "System, Method, and Non-Transitory Computer-Readable Storage Media for Generating Data for Use in Computer Systems".

U.S. Appl. No. 15/009,436, filed Jan. 28, 2016 Entitled "System, Method, and Non-Transitory Computer-Readable Storage Media for Generating Data for Use in Computer Systems".

U.S. Appl. No. 15/009,654, filed Jan. 28, 2016 Entitled "System, Method, and Non-Transitory Computer-Readable Storage Media for Creating a Meal Plan".

U.S. Appl. No. 15/009,561, filed Jan. 28, 2016 Entitled "System, Method, and Non-Transitory Computer-Readable Storage Media for Generating Accounts for Use in Computer Systems".

U.S. Appl. No. 15/009,454, filed Jan. 28, 2016 Entitled "System, Method, and Non-Transitory Computer-Readable Storage Media for Generating Data for Use in Computer Systems".

U.S. Appl. No. 15/009,583, filed Jan. 28, 2016 Entitled "System, Method, and Non-Transitory Computer-Readable Storage Media for Secure Discrete Communication with Pharmacist of Retail Store".

U.S. Appl. No. 15/009,611, filed Jan. 28, 2016 Entitled "System, Method, and Non-Transitory Computer-Readable Storage Media for Mobile Check-In in Retail Store".

U.S. Appl. No. 15/009,634, filed Jan. 28, 2016 Entitled "System, Method, and Non-Transitory Computer-Readable Storage Media for Mobile Check-Out in Retail Store".

U.S. Appl. No. 15/009,644, filed Jan. 28, 2016 Entitled "System, Method, and Non-Transitory Computer-Readable Storage Media for Evaluating Search Results in a Customer Queueing System".

Website: www.blueapron.com—Blue Apron: Fresh Ingredients, Original Recipes, Delivered to You; downloaded Feb. 3, 2016; 29 pages total. Feb. 3, 2016.

* cited by examiner

| User ID | Drug ID | Prescription Drug | Category | Dosage | No. of Refills |
|---|---|---|---|---|---|
| Alice011 | Drug001 | Albuterol | Bronchodilator | 200 mcg | 2 |
| | Drug005 | Benadryl | Antihistamines | 25mg | 12 |
| Barbara003 | Drug012 | Captopril | Ace Inhibitor | 12.5mg | 5 |
| Carl004 | Drug020 | Digoxin | Glycosides | 750 mcg | 2 |

FIG. 11

SYSTEM, METHOD, AND NON-TRANSITORY COMPUTER-READABLE STORAGE MEDIA FOR ENDLESS AISLE OF PRODUCTS IN RETAIL STORE

COPYRIGHT NOTICE

The figures included herein contain material that is subject to copyright protection. The copyright owner has no objection to the facsimile reproduction by anyone of this patent document as it appears in the U.S. Patent and Trademark Office, patent file or records, but reserves all copyrights whatsoever in the subject matter presented herein.

BACKGROUND OF THE INVENTION

1. Field of the Invention

The present invention relates generally to aisles in retail stores and, more particularly, to a system, method, and non-transitory computer-readable storage media for an endless aisle of products in a retail store.

2. Description of the Related Art

It is known that a large retailer typically has a number of retail stores with items or products stocked in the retail stores. Many consumers visit a specific retail store when shopping for products, for example, groceries, office supplies, household wares, etc. Typically, the specific retail store may have thousands of sections and hundreds of aisles for the products. Accordingly, traversing these aisles looking for specific products may be a harrowing experience. In addition, it is known that when customers cannot find the products that they are looking for, the retail store is losing significant revenue because these customers cannot find the products that they want to buy.

With so many brands of a product and different products offered for sale within a retail store, it can be difficult for a customer to find a specific product within the retail store. Further, when the customer goes to the retail store and discovers that the product is out of stock/unavailable or not carried in the retail store, they have two options. One option is to ask a sales associate for help who can assist with ordering but there is no way to track this path. The sales associate may find the product in-store or order on a multi-purpose terminal to browse .com inventory. The second option is, if they are already there, they can browse and order using the retailer's website, either while in-store using their personal mobile computing device or after leaving the retail store. This requires an additional purchase if they are also purchasing items in the retail store.

Further, customers do not have a way to order products that are out of stock or unavailable at a particular or local retail store. In addition, customers may want to see the full assortment of products that the retailer carriers beyond what is offered at the particular or local retail store. In addition, some customers may be willing to wait a few days to get the product shipped to either their local retail store or home. As a result, the retailer is losing sales because of out of stock/unavailable products in the retail store and there is no easy way for customers to order those out of stock products.

It is, therefore, desirable to provide a new system, method, and non-transitory computer-readable storage media that provides for an endless aisle of products for a retail store. It is also desirable to provide a new system, and non-transitory computer-readable storage media that enables customers to easily buy items not in stock or unavailable in their local retail store through their personal mobile computing device or through a sales associate-assisted retail store computing device with a single check out at a register or online. It is further desirable to provide a new system, and non-transitory computer-readable storage media that enables a customer to find a product that is not on a shelf of an aisle in a retail store or a variant (e.g., different color, different size, etc.) of the product for the retail store. Thus, there is a need in the art to provide a system, and non-transitory computer-readable storage media for an endless aisle of products in a retail store that meets at least one of these desires.

Many pharmacy consumers are prescribed multiple medications to take daily, particularly those who are elderly and/or those suffering from chronic medical conditions. Such consumers often have problems adhering to a medication schedule. Non-adherence to a medication schedule may have a variety of causes, including the patient forgetting to take a dose, failing to timely refill a prescription, or misunderstanding dosing instructions. Failure to adhere to a medication schedule as prescribed results in missed doses of medication(s), resulting in lower efficacy or inefficacy of medications, which may cause adverse health effects and even death. In addition, medication non-adherence may lead to increased health care costs over time.

Many pharmacy consumers desire to obtain information related to the pharmaceutical medications being prescribed to them remotely, e.g., on-line, through the Internet, or using a specially designed application or app on a personal computer or mobile device, such as a tablet or cell phone. At least some known web hosting systems include information associated with pharmaceutical drugs including treated illnesses and potential side effects. However, many of the systems do not address medication adherence issues, nor do they provide personalized information about prescribed medications.

SUMMARY OF THE INVENTION

In different embodiments of the present invention, systems, methods, and non-transitory computer-readable storage media for generating, communicating, and displaying information to users via mobile computing devices.

Accordingly, the present invention provides a system including a computer system configured to receive input from a mobile computing device and to provide output to the mobile computing device. The computer system is also configured to receive a selected product to be located in a retail store of a retailer inputted by a user into a mobile computer application running on the mobile computing device, to perform a search for the selected product on a plurality of products records corresponding to a plurality of products offered by the retailer, and to identify one or more of the product records relevant to the selected product. The computer system is configured to transmit the one or more product records identified as one or more search results, to provide the one or more search results to the mobile computer application running on the mobile computing device, each of the one or more search results being associated with a product offered by the retailer, and to suggest at least one related product to the selected product. The computer system is further configured to receive at least one product or at least one related product from the search results selected by the user using the mobile computer application running on the mobile computing device to be shipped to an address of the retail store or another address inputted by the user.

In addition, the present invention provides a method including the steps of receiving, by a computer system, a selected product to be located in a retail store of a retailer inputted by a user into a mobile computer application running on a mobile computing device, performing a search, by the computer system, for the selected product on a plurality of products records corresponding to a plurality of products offered by the retailer, and identifying, by the computer system, one or more of the product records relevant to the selected product. The method also includes the steps of transmitting, by the computer system, the one or more product records identified as one or more search results, providing, by the computer system, the one or more search results to the mobile computer application running on the mobile computing device, each of the one or more search results being associated with a product offered by the retailer, and suggesting, by the computer system, at least one related product to the selected product. The method further includes the steps of receiving, by the computer system, at least one product or at least one related product from the search results selected by the user using the mobile computer application running on the mobile computing device to be shipped to an address of the retail store or another address inputted by the user.

Further, the present invention provides one or more non-transitory computer-readable storage media, having computer-executable instructions embodied thereon, wherein when executed by at least one processor. The computer-executable instructions cause the processor to receive a selected product to be located in a retail store of a retailer inputted by a user into a mobile computer application running on a mobile computing device, perform a search for the selected product on a plurality of products records corresponding to a plurality of products offered by the retailer, and identify one or more of the product records relevant to the selected product. The computer-executable instructions also cause the processor to transmit the one or more product records identified as one or more search results, provide the one or more search results to the mobile computer application running on the mobile computing device, each of the one or more search results being associated with a product offered by the retailer, and suggest at least one related product to the selected product. The computer-executable instructions further cause the processor to receive at least one product or at least one related product from the search results selected by the user using the mobile computer application running on the mobile computing device to be shipped to an address of the retail store or another address inputted by the user.

One advantage of the present invention is that a new system, method, and non-transitory computer-readable storage media is provided for an endless aisle of products for a retail store of a large retailer. Another advantage of the present invention is that the system, method, and non-transitory computer-readable storage media enables customers to easily buy items not in stock or unavailable in a retail store through their personal mobile computing device or through a sales associate-assisted retail store computing device with a single check out at a register or online. Yet another advantage of the present invention is that the system, method, and non-transitory computer-readable storage media enables a customer to find a product that is not on a shelf or a variant of the product for the retail store. Still another advantage of the present invention is that the system, method, and non-transitory computer-readable storage media enables customers to purchase selected products or suggested products offered by the retailer and have them shipped to a retail store or their home.

Other features and advantages of the present invention will be readily appreciated, as the same becomes better understood, after reading the subsequent description taken in conjunction with the accompanying drawings.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

FIG. 11 is an illustration of exemplary database records generated by the system of FIG. 8, according to embodiments of the present invention.

Figure 1:
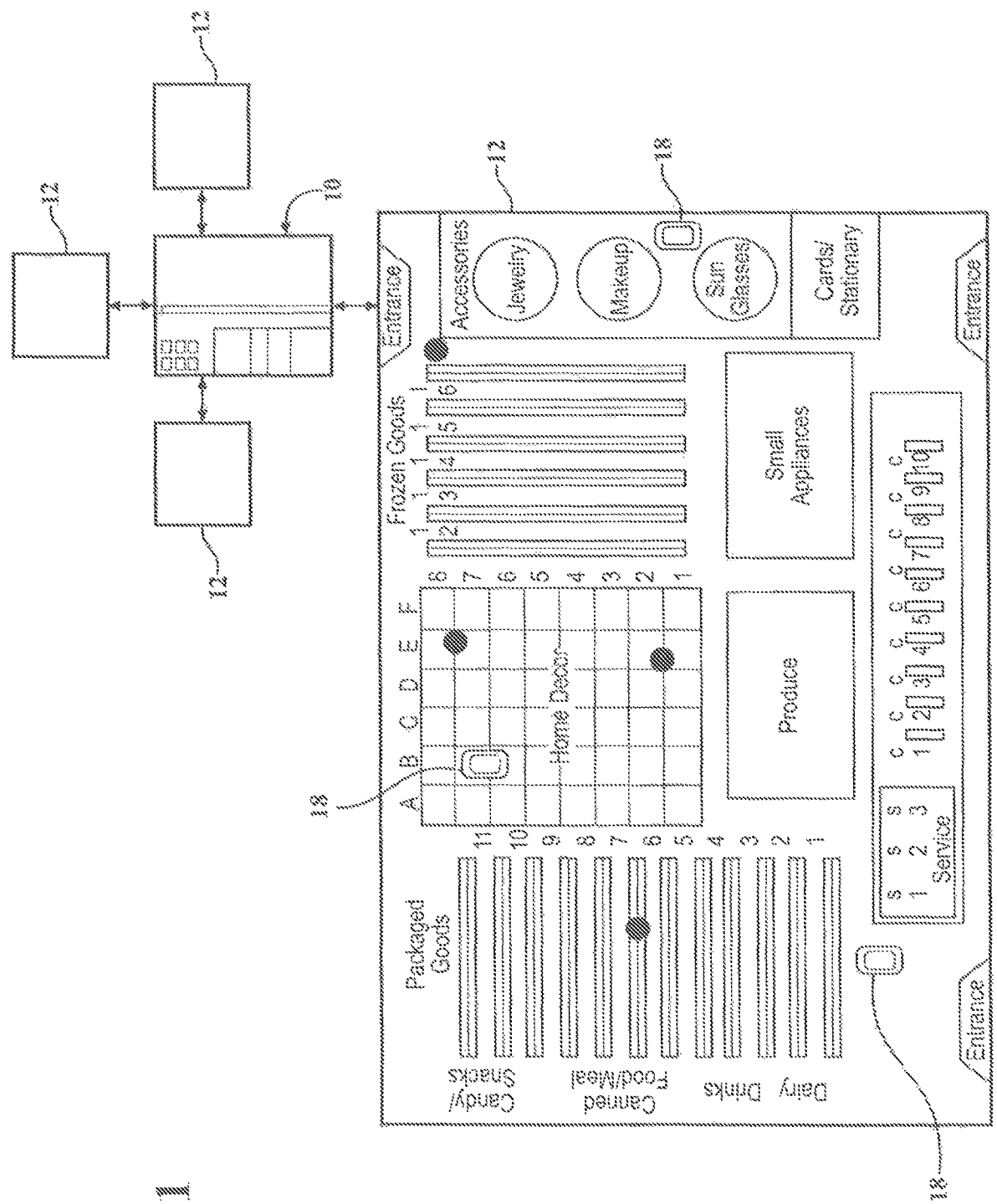
FIG. 1 is a diagrammatic view of a system, according to one embodiment of the present invention, illustrated in relationship with a retail store and at least one mobile computing device of a customer.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

DETAILED DESCRIPTION OF THE PREFERRED EMBODIMENT(S)

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

Reference throughout this specification to "one embodiment", "an embodiment", "one example" or "an example" means that a particular feature, structure or characteristic described in connection with the embodiment or example is included in at least one embodiment of the present invention. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

Embodiments in accordance with the present invention may be embodied as an apparatus, method, or computer program product. Accordingly, the present invention may take the form of an entirely hardware embodiment, an entirely software embodiment (including firmware, resident software, micro-code, etc.), or an embodiment combining software and hardware aspects that may all generally be referred to herein as a "module" or "system." Furthermore, the present invention may take the form of a computer program product embodied in any tangible media of expression having computer-usable program code embodied in the media.

Any combination of one or more computer-usable or computer-readable media (or medium) may be utilized. For example, a computer-readable media may include one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present invention may be written in any combination of one or more programming languages.

Embodiments may also be implemented in cloud computing environments. In this description and the following claims, "cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

The flowchart and block diagrams in the flow diagrams illustrate the architecture, functionality, and operation of possible implementations of systems, methods, and computer program products according to various embodiments of the present invention. In this regard, each block in the flowchart or block diagrams may represent a module, segment, or portion of code, which includes one or more executable instructions for implementing the specified logical function(s). It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions. These computer program instructions may also be stored in a computer-readable media that can direct a computer or other programmable data processing apparatus to function in a particular manner, such that the instructions stored in the computer-readable media produce an article of manufacture including instruction means which implement the function/act specified in the flowchart and/or block diagram block or blocks.

Several (or different) elements discussed below, and/or claimed, are described as being "coupled", "in communication with", or "configured to be in communication with". This terminology is intended to be non-limiting, and where appropriate, be interpreted to include without limitation, wired and wireless communication using any one or a plurality of a suitable protocols, as well as communication methods that are constantly maintained, are made on a periodic basis, and/or made or initiated on an as needed basis.

The disclosure particularly describes how a large retailer may provide an endless aisle of products for a retail store of the retailer. Particularly, the present disclosure describes how a system, method, and non-transitory computer-readable storage media enables customers to easily buy items not in stock or unavailable in the retail store through their personal mobile computing device or through a sales associate-assisted retail store computing device with a single check out at a register or online and have them shipped to the retail store or their home.

With reference to the FIGS. and in operation, the present invention provides a system 10, method, and computer product media that facilitate an endless aisle of products for a retail store of a retailer. In particular, the present invention facilitates customers to easily buy items/products not in stock or unavailable in the retail store through their personal mobile computing device or through a sales associate-assisted retail store computing device with a single check out at a register or online and have them shipped to the retail store or their home.

Referring to FIG. 1, an exemplary environment in which the system 10 for an endless isle of products for a retail store 12 of a retailer, according to the present invention, operates is illustrated. The system 10 may be configured for a large retailer having one or more retail stores 12 each having one or more items or products in the retail stores 12. The term "retail store" can include brick-and-mortar stores operated by a single retailer, e.g., supermarket or superstore, or a location that includes stores operated by multiple retailers, e.g., a shopping mall or a shopping plaza.

The exemplary retail store 12 illustrated in FIG. 1 can be arranged into different departments, such as packaged goods including dairy, drinks, canned foods/meals, and candy/snacksproduce; home decor; produce; frozen goods; small appliances; and accessories including jewelry, make-up, sunglasses, and cards/stationary. Each department can be further delineated. For example, the exemplary packaged goods area of the retail store 12 can be subdivided into aisles 1-11 and each aisle can define an "a" side and a "b" side opposite the "a" side. The exemplary home decor area can be divided into a grid by letters A-F along a first edge and numbers 1-8 along a second edge perpendicular to the first edge. The illustrated, exemplary retail store 12 can also include one or more entrances, a service counter, and several checkout lines each referenced in FIG. 1 by the letter "c" and a number. It should be appreciated that the arrangement of the retail store 12 is exemplary. It should also be appreciated that, in some embodiments of the present invention, the retail store 12 can be arranged differently and include different departments and/or different products and/or methods for labeling aisles.

Figure 2:
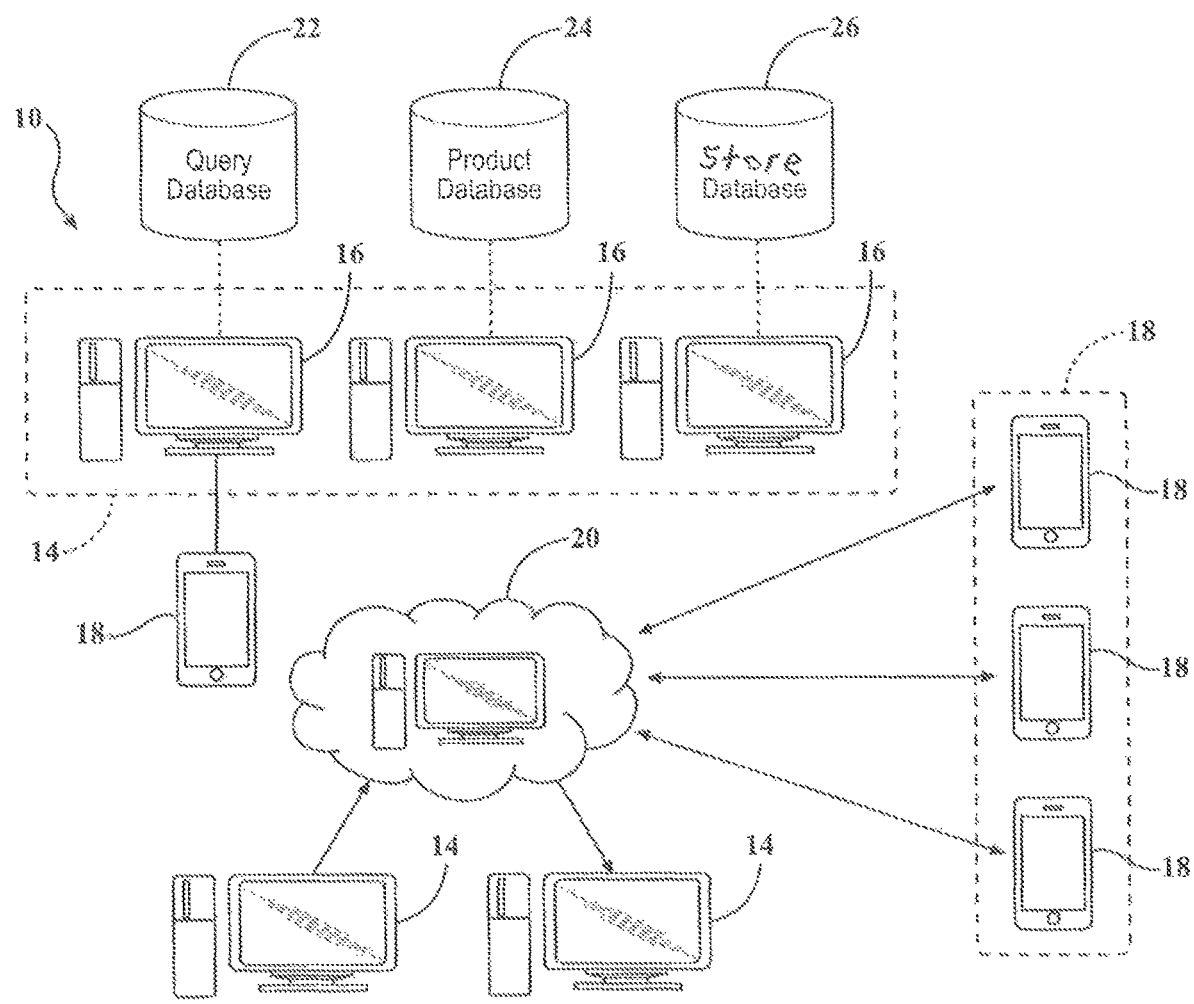
FIG. 2 is another diagrammatic view of the system of FIG. 1.

Referring to FIG. 2, the system 10 may include one or more server systems 14 that may each be embodied as one or more server computers 16 each including one or more processors that are in data communication with one another. The server system 14 may be in data communication with one or more customer computing devices. In the system 10 and method disclosed herein, the customer computing devices may be embodied as mobile computing devices 18 such as desktop computers or other computing devices such as a mobile phone, tablet computer, smartphone/tablet computer hybrid, a personal data assistant, a handheld mobile device including a cellular telephone, and the like.

For clarity in discussing the various functions of the system 10, multiple computers and/or servers are discussed as performing different functions. These different computers (or servers) may, however, be implemented in multiple different ways such as modules within a single computer, as nodes of a computer system, etc . . . . The functions as performed by the system 10 (or nodes or modules) may be centralized or distributed in any suitable manner across the system 10 and its components, regardless of the location of specific hardware. Furthermore, specific components of the system 10 may be referenced using functional terminology in their names. The function terminology is used solely for purposes of naming convention and to distinguish one element from another in the following discussion. Unless otherwise specified, the name of an element conveys no specific functionality to the element or component.

Some or all of the server systems 14, servers, or server computers 16 and customer computing devices or mobile computing devices 18 may communicate with one another by means of a network 20. The network 20 may be embodied as a peer-to-peer connection between devices, a connection through a local area network (LAN), WiFi network, the Internet, or any other communication medium or system. Each of the server systems 14 or server computers 16 may be coupled to one another by separate networks or some or all of the server systems 14 or server computers 16 may share a common network. For example, in some embodiments, the server systems 14 or server computers 16 may communicate over a separate private network, rather than over the network 20. It should be appreciated that the user computing device such as the mobile computing device 18, as well as any other connected computer systems and their components included in the system 10, can create message related data and exchange message related data (e.g., near field communication ("NFC") payloads, Bluetooth packets, Internet Protocol ("IP") datagrams and other higher layer protocols that utilize IP datagrams, such as, Transmission Control Protocol ("TCP"), Hypertext Transfer Protocol ("HTTP"), Simple Mail Transfer Protocol ("SMTP"), etc.) over the network 20.

Figure 3:
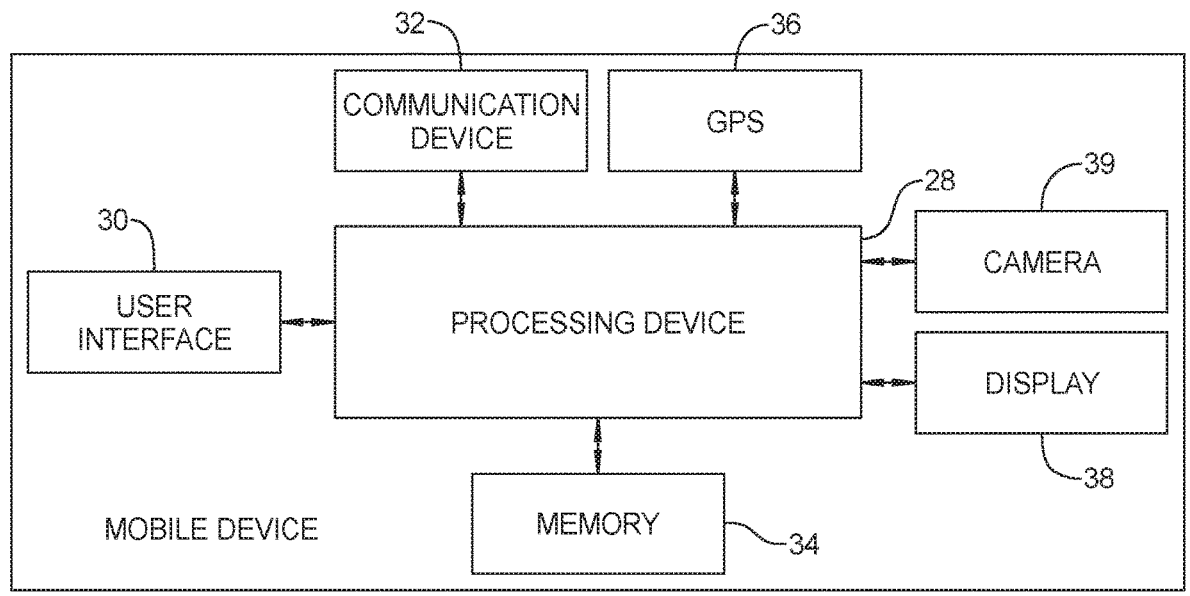
FIG. 3 is a diagrammatic view of a mobile computing device used with the system of FIG. 1.

Referring now to FIG. 3, a schematic illustrating example components of one mobile computing device 18 of FIG. 1 is illustrated. In the illustrative embodiment, the mobile computing device 18 includes a processing device 28, a user interface 30, a communication device 32, a memory device 34, a global positioning system (GPS) 36, a display 38, and a camera 39. It should be appreciated that the mobile computing device 18 can include other components and some of the components are not required. It should be appreciate that, in one embodiment, a user computing device includes the mobile computing device 18 such as, for example, a smartphone such as an iPhone™ and may include a Wi-Fi antenna, a cellular network antenna, a Bluethooth' communications device, assisted GPS and GLONASS, a digital compass, and an iBeacon microlocation device.

The processing device 28 can include memory, e.g., read only memory (ROM) and random access memory (RAM), storing processor-executable instructions and one or more processors that execute the processor-executable instructions. In embodiments where the processing device 28 includes two or more processors, the processors can operate in a parallel or distributed manner. The processing device 28 can execute the operating system of the mobile computing device 18.

The user interface 30 is a device that allows a user to interact with the mobile computing device 18. While one user interface 30 is shown, the term "user interface" can include, but is not limited to, a touch screen, a physical keyboard, a mouse, a microphone, and/or a speaker. The communication device 32 is a device that allows the mobile computing device 18 to communicate with another device, e.g., the server system 14 or server computer 16, via the network 20. The communication device 32 can include one or more wireless transceivers for performing wireless communication and/or one or more communication ports for performing wired communication. The memory device 34 is a device that stores data generated or received by the mobile computing device 18. The memory device 34 can include, but is not limited to, a hard disc drive, an optical disc drive, and/or a flash memory drive.

The GPS 36 is a device that determines a location of the mobile computing device 18 by communicating with a plurality of GPS satellites. The GPS 36 can perform known triangulation techniques to determine the GPS coordinates of the mobile computing device 18. It should be appreciated that while a GPS 36 is shown, any other suitable component for determining the location of the mobile computing device 18 can be implemented.

The display 38 of the mobile computing device 18 may be a graphical user interface (GUI) that displays a mobile computer application and search results of the retailer. The GUI further includes a plurality of input objects which allow the user to provide commands to the mobile computing device 18. It should be appreciated that, in some embodiments, the user interface 30 and the display 38 may be one in the same.

The camera 39 of the mobile computing device 18 may be a device capturing view on the rear of the device 18. The rear facing camera 39 can monitor a video feed for a recognizable pattern, such as UPC code. A scan can be executed based upon any readable barcode being visible in the view of the camera 39. If more than one code is available to scan, the camera 39 can take a dominant code, for example, closest to the center of the display or the camera 39 can signal to the user that conditions are too ambiguous to execute a scan. Scanning of an item/product can require that the code be scanned to fill most of a view captured by the camera 39. In another embodiment, the user can be presented with a reticle or graphic indicating a region of the display that the user should put the code to be scanned within for the scan to execute. It should be appreciated that the camera 39 is conventional and interfaces with the processing device 28.

Referring again to FIG. 2, the server system 14 may be associated with a retailer, or other entity, providing search services. For example, the server system 14 may host a search engine or a site hosted by a retailer to provide access to information about products and user opinions about products. For example, the server system 14 may host or access a query database 22, product database 24, and store database 26, which may be coupled to the server system 14 or server computers 16.

The system 10 described herein may make use of data known about queries and user responses to queries. Accordingly, the server system 14 may host or access the query database 22 of queries. A record for a query may include product click data for a particular query. Product click data may additionally or alternatively include impression data. For example, a record of a query may include a record of the product records returned as a result for the query and an indication of which of the product records were actually selected by the query's author. In some embodiments, for each brand record of a plurality of brands, impressions for the brand (e.g. a number of times product records corresponding to the brand have been included in search results to a query) and click data for the brand (e.g. a number of times product records corresponding to the brand were selected from among search results) may be compiled for the queries and associated with the product record.

The system 10 described herein may make use of product data for products either located in the retail store 12 or offered by the retailer. Accordingly, the server system 14 may host or access the product database 24 of products either located in the retail store 12 or offered by the retailer on-line or other retail stores. The product database 24 may store a plurality of product records. The product records may have one or more brands associated therewith. A brand for a product may represent the manufacturer, seller, importer, or the like for a product and/or a manufacturer of a component part of a product, or other reference to an entity participating in the production and offer for sale of a product.

The system 10 described herein may make use of location data for a location of the retail store 12. Accordingly, the server system 14 may host or access the store database 26 for a location of the retail store 12. The store database 26 may store a plurality of locations for a plurality of retail stores 12. It should be appreciated that each location of each retail store 12 may be determined by GPS.

Figure 4:
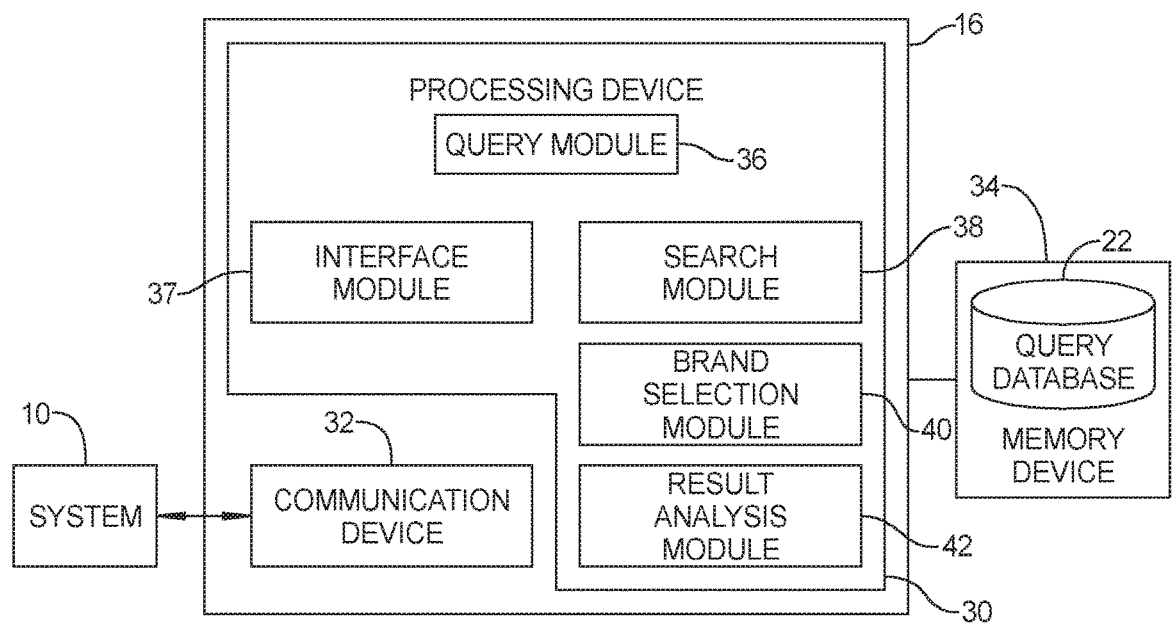
FIG. 4 is a diagrammatic view of one portion of the system of FIG. 1.

Referring to FIG. 4, the server computer 16 for querying the query database 22 may be configured to perform one or more functions at the request of the mobile computing device 18. In the illustrated embodiment, the query server computer 16 may include a processing device 30, a communication device 32, and memory device 34.

The processing device 30 can include memory, e.g., read only memory (ROM) and random access memory (RAM), storing processor-executable instructions and one or more processors that execute the processor-executable instructions. In embodiments where the processing device 30 includes two or more processors, the processors can operate in a parallel or distributed manner. In the illustrative embodiment, the processing device 30 executes one or more of a query module 36, an interface module 37, a search module 38, a brand determination module 40, and a result analysis module 42.

The communication device 32 is a device that allows the query server computer 16 to communicate with another device, e.g., the mobile computing device 18, via the network 20. The communication device 32 can include one or more wireless transceivers for performing wireless communication and/or one or more communication ports for performing wired communication. The communication device 32 is accessible to the processing device 30.

The memory device 34 is a device that stores data generated or received by the query server computer 16. The memory device 34 can include, but is not limited to a hard disc drive, an optical disc drive, and/or a flash memory drive. Further, the memory device 34 may be distributed and located at multiple locations. The memory device 34 is accessible to the processing device 30. In some embodiments, the memory device 34 stores the query database 22.

The query module 36 includes software and/or hardware modules implementing searching methods disclosed herein. In some embodiments, the modules and data of the query module 36 are implemented or accessed by the server system 14, query server computer 16, or some other entity that provides an interface to the query module 36.

The query module 36 may include the interface module 37 for receiving queries and transmitting responses to queries to a requesting entity. The interface module 37 may be part of a data flow such that a query input to the query module 36 is not received directly from, for example, the mobile computing device 18. For example, a query may be expanded or otherwise modified to include keywords associated with concepts identified in the query. The query may also be generated by some other software module executed by the server system 14. Whichever entity originated a query received by the interface module 37, the interface module 37 may route the search results to this requesting entity or to some other entity specified with the query.

The query module 36 may include the search module 38 that may search a corpus of documents, such as a database of product records, over the Internet, or other corpus and return results relevant to a particular query. The search module 38 may implement any search algorithm, e.g. search engine, known in the art for identifying documents relevant to a query, from a simple keyword matching search to a more complex search with word sense disambiguation, contextual searching, or other strategy for identifying relevant documents.

The query module 36 may also include the brand selection module 40 that may select brands for use in one or both of filtering search results, organizing search results, and presenting search results to users. The brand selection module 40 may select brands corresponding to the product queried that are either physically located in the retail store 12 or offered by the retailer on-line or in other retail stores using outputs from the result analysis module 42.

The query module 36 may also include the result analysis module 42. The brands that are useful in identifying relevant search results may be determined in part based on a composition of search results, specifically the number of product records corresponding to each brand present in the search results. Accordingly, the result analysis module 42 may evaluate search results in order to facilitate this determination.

Figure 5:
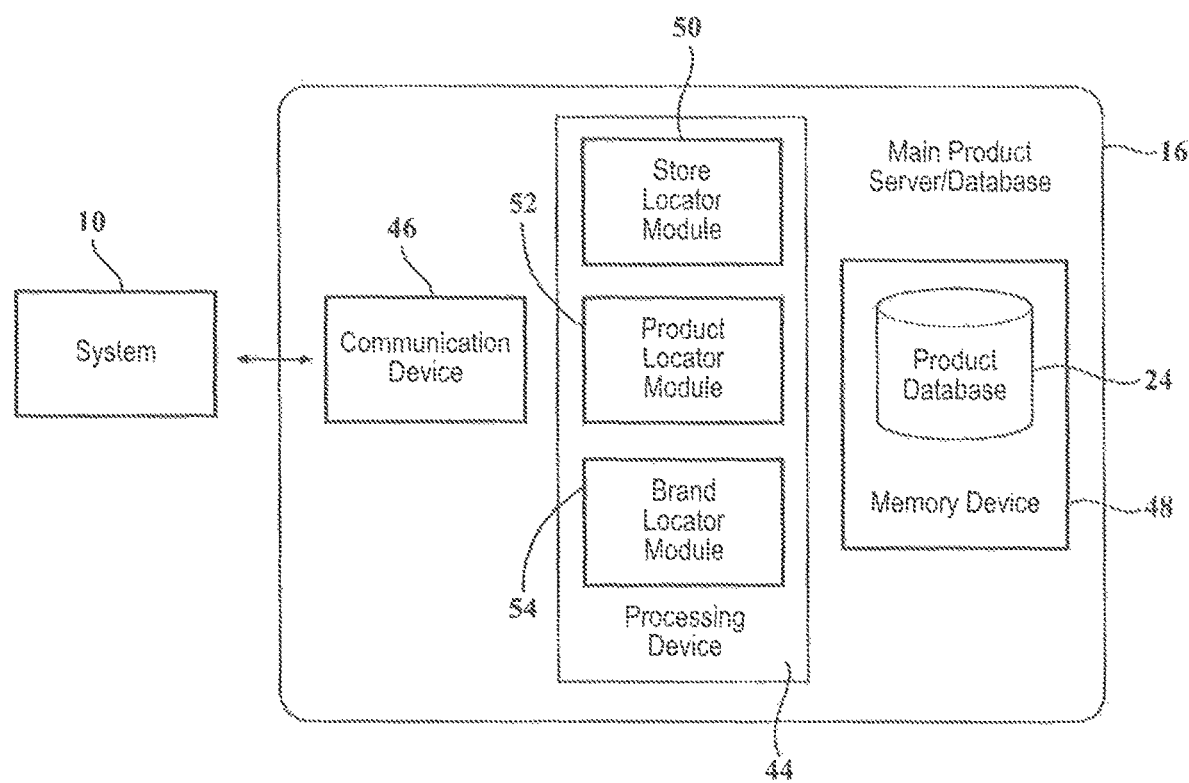
FIG. 5 is a diagrammatic view of another portion of the system of FIG. 1.

Referring to FIG. 5, the main product server computer 16 for accessing the main product database 24 may be configured to perform one or more functions at the request of the mobile computing device 18. The product server 16 may be configured to perform one or more of the requested functions. In the illustrated embodiment, the product server 16 may include a processing device 44, a communication device 46, and memory device 48. It should be appreciated that the main product database 24 communicates with individual store product databases and a retailer on-line database and is updated from them. It should also be appreciated that the main product database 24 can be updated by either polling the store product databases and the retailer on-line database as a set frequency or by allowing the store product databases and retailer on-line database to push updates directly to the main product database 24. It should further be appreciated that, in other embodiments, the system 10 could query the actual store product database and retailer on-line database itself instead of the main product database 24.

The processing device 44 can include memory, e.g., read only memory (ROM) and random access memory (RAM), storing processor-executable instructions and one or more processors that execute the processor-executable instructions. In embodiments where the processing device 44 includes two or more processors, the processors can operate in a parallel or distributed manner. In the illustrative embodiment, the processing device 44 executes one or more of a store locator module 50, a product locator module 52, and a brand locator module 54.

The communication device 46 is a device that allows the product server 16 to communicate with another device, e.g., query server computer 16, store server computer 16, and/or the mobile computing device 18, via the network 20. The communication device 46 can include one or more wireless transceivers for performing wireless communication and/or one or more communication ports for performing wired communication. The communication device 46 is accessible to the processing device 44.

The memory device 48 is a device that stores data generated or received by the product server computer 16. The memory device 48 can include, but is not limited to a hard disc drive, an optical disc drive, and/or a flash memory drive. Further, the memory device 48 may be distributed and located at multiple locations. The memory device 48 is accessible to the processing device 44. In some embodiments, the memory device 44 stores the product database 24.

In some embodiments, the memory device 48 stores a retail store location database that can store the retail store locations of one or more retail stores 12 operated or associated with a retailer. The retail store location database may be queried using a specific location, e.g., GPS coordinates, or a general location, e.g., postal zip code or city/state, and can return one or more retail stores 12 that are proximate to the specific or general location.

The product database 24 may further store a type of each product sold by the retailer, e.g., groceries, home decor, and personal goods, and/or a section of the product, e.g., dairy or men's clothing. Furthermore, the types and/or sections can be stored either relative to each store location or offered on-line by the retailer. In this way, the product database 24 can be queried with a store location of a retail store 12 or retailer on-line database and can return a type or brand of the product either at the store location of the retail store 12 or offered on-line by the retailer.

As discussed, the processing device 44 may execute the store locator module 50. The store locator module 50 receives a location from the mobile computing device 18 and determines one or more store locations of the retail stores 12 corresponding to the received location. In some embodiments, the store locator module 50 queries the store location database with the received location and receives the store location of the retail store 12 that correspond to the received location. When more than one store location is received, the store locator module 50 may automatically select the store location nearest to the received location or may provide the store locations to the mobile computing device 18, thereby allowing the mobile computing device 18 or the user or customer to select the store location of the retail store 12. It should be appreciated that the user or customer can choose their store location/address as well in case that they want to search a retail store different from the location the mobile computing device 18 is providing or if the mobile computing device 18 is not returning a store location.

The product locator module 52 receives an input of a product to be located either in the retail store 12 or by the retailer on-line and determines products corresponding to one or more items or products. In some embodiments, the product locator module 52 for the product queries the product database 24 with the product and a store location (which may have been determined by the store locator module 50) or the retailer on-line product database and receives a location of the product in a retail store 12 or that the product is offered on-line by the retailer. The mobile computing device 18 can display the products in the electronic list of the search results for the selected product.

Figure 6:
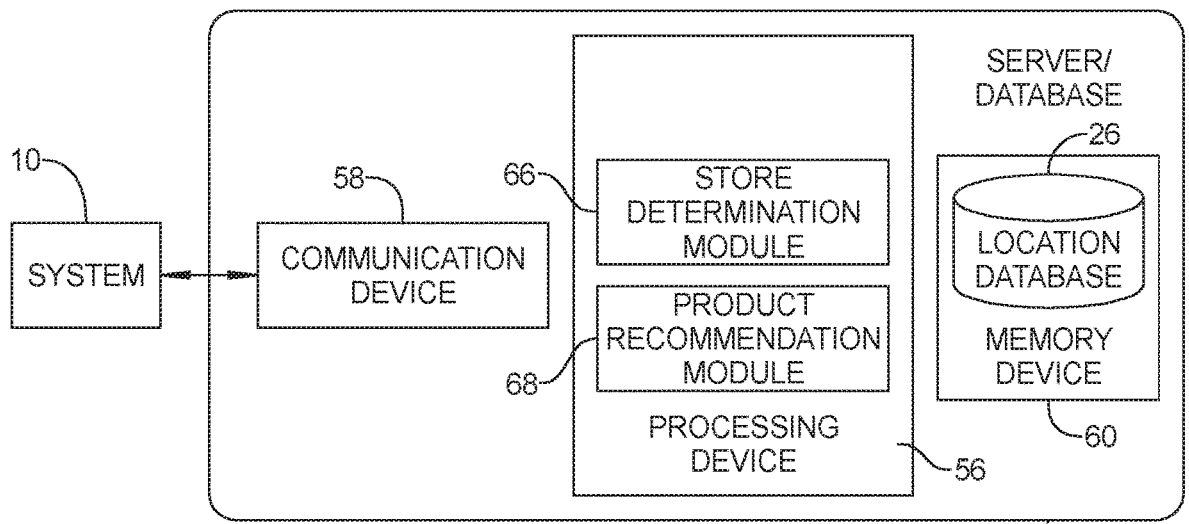
FIG. 6 is a diagrammatic view of yet another portion of the system of FIG. 1.

Referring now to FIG. 6, an example of the store server computer 16 accessing the store database 26 is illustrated. In the illustrated example, the store server computer 16 includes, but is not limited to, a processing device 56, a communication device 58, and a memory device 60.

The processing device 56 can include memory, e.g., read only memory (ROM) and random access memory (RAM), storing processor-executable instructions and one or more processors that execute the processor-executable instructions. In embodiments where the processing device 56 includes two or more processors, the processors can operate in a parallel or distributed manner. In the illustrative embodiment, the processing device 56 executes one or more of a store determination module 66 and a product recommendation module 68.

The communication device 58 is a device that allows the store server computer 16 to communicate with another device, e.g., the server system 14, the server computers 16, and/or the mobile devices 18, via the communication network 20. The communication device 58 can include one or more wireless transceivers for performing wireless communication and/or one or more communication ports for performing wired communication. The communication device 58 is accessible to the processing device 56.

The memory device 60 can be any device that stores data generated or received by the store server computer 16. The memory device 60 can include, but is not limited to a hard disc drive, an optical disc drive, and/or a flash memory drive. Further, the memory device 60 may be distributed and located at multiple locations. The memory device 60 is accessible to the processing device 56. In some embodiments, the memory device 60 stores the store database 26.

The product recommendation module 68 determines at least one or more suggested or recommended products based on the selected product queried, each suggested/recommended product being indicative of an item or product either sold at the location of the retail store 12 or on-line by the retailer. The suggested/recommended products are determined from an algorithm in the product recommendation module 68 based on the product in the search query.

In operation, the store determination module 66 can determine a store location of the customer. Based on the store location, the store determination module 66 can obtain an address corresponding to the store location.

The system 10 links the server systems 14 or server computers 16 to transmit and provide the one or more search results as a list to the mobile computing device 18. Each of the one or more search results is a name of a brand or specific product and is associated with either a physical location of the product in the retail store 12 or offered on-line by the retailer.

Other features of the system 10 can be found in the following commonly owned US patent applications, which are hereby incorporated by reference: U.S. patent application Ser. No. 15/009,327, filed on Jan. 28, 2016; U.S. patent application Ser. No. 15/009,374, filed on Jan. 28, 2016; U.S. patent application Ser. No. 15/009,417, filed on Jan. 28, 2016; U.S. patent application Ser. No. 15/009,561, filed on Jan. 28, 2016; U.S. patent application Ser. No. 15/009,436, filed on Jan. 28, 2016; U.S. patent application Ser. No. 15/009,654, filed on Jan. 28, 2016; U.S. patent application Ser. No. 15/009,583, filed on Jan. 28, 2016; U.S. patent application Ser. No. 15/009,454, filed on Jan. 28, 2016; U.S. patent application Ser. No. 15/009,611, filed on Jan. 28, 2016; U.S. patent application Ser. No. 15/009,634, filed on Jan. 28, 2016; and, U.S. patent application Ser. No. 15/009,644, filed on Jan. 28, 2016.

Figure 7:
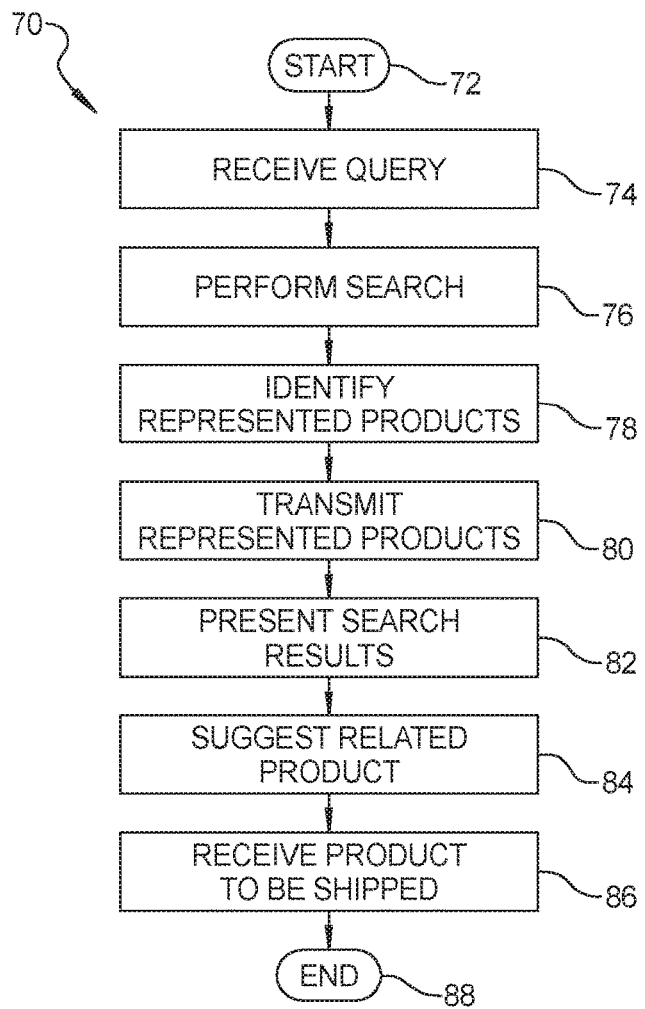
FIG. 7 is a flowchart of a method, according to one embodiment of the present invention, of using the system of FIGS. 1 through 6.

Referring now to FIG. 7, an example method 70, according to one embodiment of the present invention, using the system 10 configured to receive input from a mobile computing device 18 and to provide to the mobile computing device 18 is illustrated. The method 70 can be executed by the components illustrated in FIGS. 1 through 6. In general, a flowchart of the method 70, according to one embodiment of the present invention, starts in bubble 72. The method 70 includes the steps of receiving, by a computer system, a selected product to be located in a retail store of a retailer inputted by a user into a mobile computer application running on the mobile computing device in block 74. For example, receiving, by the system 10, a search query for a product to be located in the retail store 12 inputted into a mobile application running on the mobile device 18 by a customer using the mobile device 18. For example, the customer scans the shelf-tag or inputs the name of the selected product (using either their personal mobile computing device or a sales associate computing device) which takes them to an expanded assortment of products of the retailer. The method 70 also includes the step of performing a search, by the computer system, for the selected product on a plurality of products records corresponding to a plurality of products offered by the retailer in block 76. For example, performing a search, by the system 10, on a plurality of products records corresponding to a plurality of products located in the retail store 12, which may include inputting the search query to any search algorithm known in the art. The corpus of documents searched may include a database of product records or some other corpus of documents, accessible over the Internet.

The method 70 includes the steps of identifying represented brands or specific products in the retail store 12 or offered on-line corresponding to the selected product queried in block 78. For example, identifying, by the computer system, one or more of the product records relevant to the selected product. For example, each brand has at least one product record corresponding to the brand, or an above-threshold number of product records corresponding thereto, may be deemed to be represented. The method 70 includes the steps of transmitting, by the computer system, the one or more product records identified as one or more search results in block 80. For example, transmitting, by the system 10, a representation of the one or more product records identified as one or more search results. The method 70 further includes providing, by the computer system, the one or more search results to the mobile computer application running on the mobile computing device, each of the one or more search results being associated with a product offered by the retailer in block 82. For example, providing, by the system 10, the one or more search results as a list to the mobile computing device 18, each of the one or more search results being associated with a product either physically located in the retail store 12 or on-line by the retailer. The method 70 also includes the step of suggesting, by the computer system, at least one related product to the selected product in block 84. For example, suggesting, by the computer system 10, at least one product related to the selected product to the mobile computing device 18 for display. The method 70 further includes the steps of receiving, by the computer system, at least one product or at least one related product from the search results selected by the user using the mobile computer application running on the mobile computing device to be shipped to an address of the retail store or another address inputted by the user in block 86. For example, from the search results, the customer can order the selected product or the suggested product for delivery (shipping will be free for the customer). The customer can pay at checkout for their entire basket (for items found in the retail store) at a sales system in the retail store 12 or pay for the item/product online from the mobile computing device 18. The method ends in block 88. It should be appreciated that the payment is handled at the point of sale so that the item/product is included in the customer's shopping cart when selected and the customer can pay at the cashier with the rest of their items/products in their physical shopping cart. It should be appreciated that the method includes other steps such as providing the computer system and servers and coupling the servers to one another.

A controller, computing device, server or computer, such as described herein, includes at least one or more processors or processing units and a system memory (see above). The controller typically also includes at least some form of computer readable media. By way of example and not limitation, computer readable media may include computer storage media and communication media. Computer storage media may include volatile and nonvolatile, removable and non-removable media implemented in any method or technology that enables storage of information, such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art should be familiar with the modulated data signal, which has one or more of its characteristics set or changed in such a manner as to encode information in the signal. Combinations of any of the above are also included within the scope of computer readable media.

The order of execution or performance of the operations in the embodiments of the invention illustrated and described herein is not essential, unless otherwise specified. That is, the operations described herein may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In some embodiments, a processor, as described herein, includes any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term processor.

In some embodiments, a database, as described herein, includes any collection of data including hierarchical databases, relational databases, flat file databases, object-relational databases, object oriented databases, and any other structured collection of records or data that is stored in a computer system. The above examples are exemplary only, and thus are not intended to limit in any way the definition and/or meaning of the term database. Examples of databases include, but are not limited to only including, Oracle® Database, MySQL, IBM® DB2, Microsoft® SQL Server, Sybase®, and PostgreSQL. However, any database may be used that enables the systems and methods described herein. (Oracle is a registered trademark of Oracle Corporation, Redwood Shores, Calif.; IBM is a registered trademark of International Business Machines Corporation, Armonk, N.Y.; Microsoft is a registered trademark of Microsoft Corporation, Redmond, Wash.; and Sybase is a registered trademark of Sybase, Dublin, Calif.).

Figure 8:
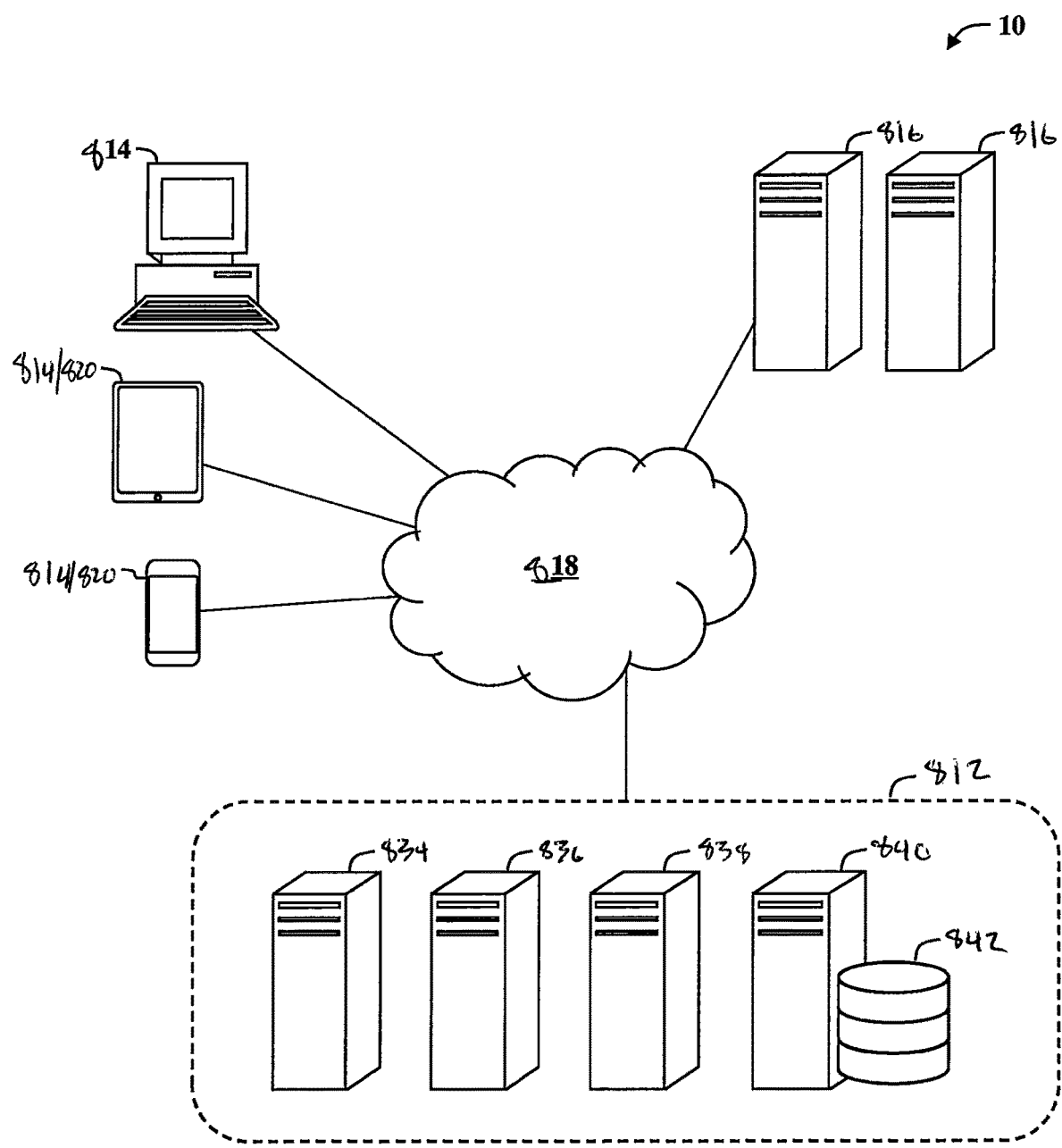
FIG. 8 is a schematic illustrating various aspects of a system, according to the present invention.

With reference to the FIGS. and in operation, the present invention provides a networked computer system 10, methods and computer product media that monitors the activities of pharmacy customers and provides notification of potential drug interactions to a user via a website. Referring to FIG. 8, an exemplary environment in which the networked computer system 10 operates is illustrated. In general, the present invention describes a networked computer system 10 that assists pharmacy customers adhere to a medication schedule and alerts the pharmacy customers about upcoming or missed doses based on the medication schedule. Moreover, the networked computer system 10 is configured to communicate with a mobile device associated with the customer to provide push notifications to the mobile devices including messages about missed or upcoming doses to the pharmacy customers. The system 10 may also include a mobile computer application being stored on a mobile device associated with the pharmacy customer.

The system 10 is configured to generate and store user pharmacy data records associated with pharmacy customers that includes information associated with pharmaceutical drugs being used by the customers. In addition, the user pharmacy data records may include triggering events that are detected by the system. The triggering events may include detecting a date and/or time that a customer is due for a medication dose, or determining that a new or updated prescription is available.

By generating triggering events that trigger corresponding system actions, the system 10 improves the speed and functionality of known computing systems by reducing the amount of computing time required to monitor customer activity, thus reducing the computing resources required to generate and display relevant pharmacy messages to pharmacy customers.

For clarity in discussing the various functions of the system 10, multiple computers and/or servers are discussed as performing different functions. These different computers (or servers) may, however, be implemented in multiple different ways such as modules within a single computer, as nodes of a computer system, etc. . . . The functions performed by the system 10 (or nodes or modules) may be centralized or distributed in any suitable manner across the system 10 and its components, regardless of the location of specific hardware. Furthermore, specific components of the system 10 may be referenced using functional terminology in their names. The function terminology is used solely for purposes of naming convention and to distinguish one element from another in the following discussion. Unless otherwise specified, the name of an element conveys no specific functionality to the element or component.

In the illustrated embodiment, the system 10 includes a server system 10112 that is coupled in communication with one or more user computing devices 10114 and one or more third party computer servers 10116 via a communications network 10118. The communications network 818 may be any suitable connection, including the Internet, file transfer protocol (FTP), an Intranet, LAN, a virtual private network (VPN), cellular networks, etc. . . . , and may utilize any suitable or combination of technologies including, but not limited to wired and wireless connections, always on connections, connections made periodically, and connections made as needed.

The user computing device 814 may include any suitable device that enables a user to access and communicate with the system 10 including sending and/or receiving information to and from the system 10 and displaying information received from the system 10 to a user. For example, in one embodiment, the user computing device 814 may include, but is not limited to, a desktop computer, a laptop or notebook computer, a tablet computer, smartphone/tablet computer hybrid, a personal data assistant, a handheld mobile device including a cellular telephone, and the like. The user computing device 814, as well as any other connected computer systems and their components included in the system 10, can create message related data and exchange message related data (e.g., near field communication ("NFC") payloads, Bluetooth packets, Internet Protocol ("IP") datagrams and other higher layer protocols that utilize IP datagrams, such as, Transmission Control Protocol ("TCP"), Hypertext Transfer Protocol ("HTTP"), Simple Mail Transfer Protocol ("SMTP"), etc.) over the network.

Figure 9:
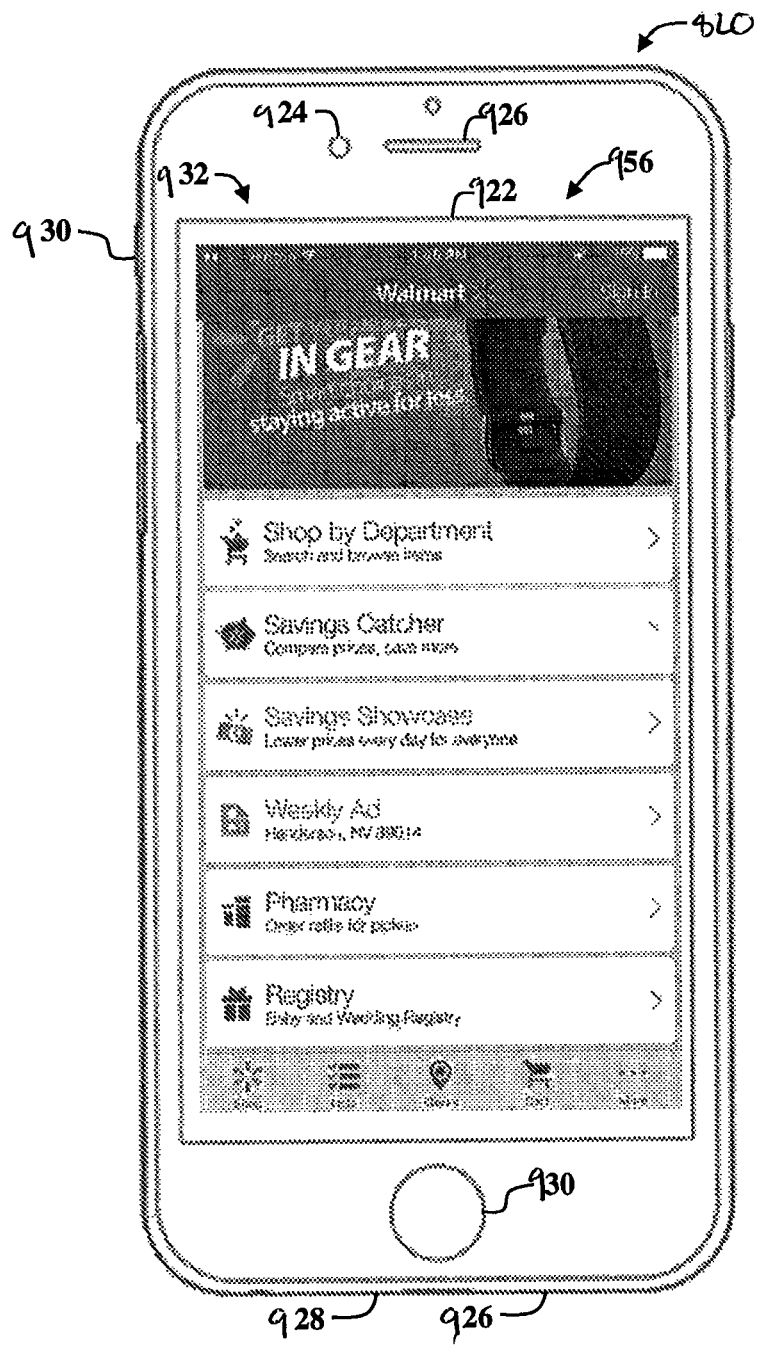
FIG. 9 is a schematic illustrating an exemplary mobile device used with the system of FIG. 8, according to an embodiment of the present invention.

Referring now to FIG. 9, in one embodiment, the user computing device includes a mobile computing device 820 such as, for example, a smartphone such as an iPhone™. The mobile computing device 820 includes a processor coupled to a memory device, and a database for storing various programs and data for use in operating the mobile computing device 820. The mobile computing device 820 may also include a touchscreen display device 922, one or more video image cameras 924, one or more speakers 926, a microphone 928, at least one input button 930, and one or more sensors including, but not limited to, a touch ID fingerprint sensor coupled to an input button 930, a barometer, a three-axis gyro, an accelerometer, proximity sensor, and an ambient light sensor. In addition, the mobile computing device 820 may also include a Wi-Fi antenna, a cellular network antenna, a Bluethooth™ communications device, assisted GPS and GLONASS, a digital compass, and an iBeacon microlocation device.

In the illustrated embodiment, the mobile computing device 820 includes a web browser programmed stored in the memory device. The processor executes the web browser program to display web pages on the touchscreen display device 922 that includes information received from the server system 10112 to enable a user to interact with and operate the server system 10112. In addition, the mobile computing device 820 may be programmed to store and execute a mobile program application, e.g. a mobile application, that displays a user interface 932 on the touchscreen display device 922 that allows the user to access the server system 10112 to retrieve and store information within the server system 10112 as well as interact with and operate the server system 10112.

Referring again to FIG. 8, the third party computer servers 816 include information and data associated with medications. For example, in one embodiment, the third party computer servers 816 may include, for a particular medication, a name, drug class, shape, color, and imprint of the pill, strength, and typical dosage instructions. It may additionally include information about side effects and drug interactions.

In the illustrated embodiment, the server system 10112 includes a website hosting server 834, a pharmacy account server 836, a search engine server 838, a database server 840, and a database 842. The database server 842 includes a memory device that is connected to the database 842 to retrieve and store information contained in the database 842. The database 842 contains information on a variety of matters, such as, for example, webpages associated with one or more websites, search queries, prescription drug information, over-the-counter (OTC) drug information, customer pharmacy account information, product records, notification messages, mobile device application program interfaces (APIs), and/or any suitable information that enables the system 10 to function as described herein.

Figure 10:
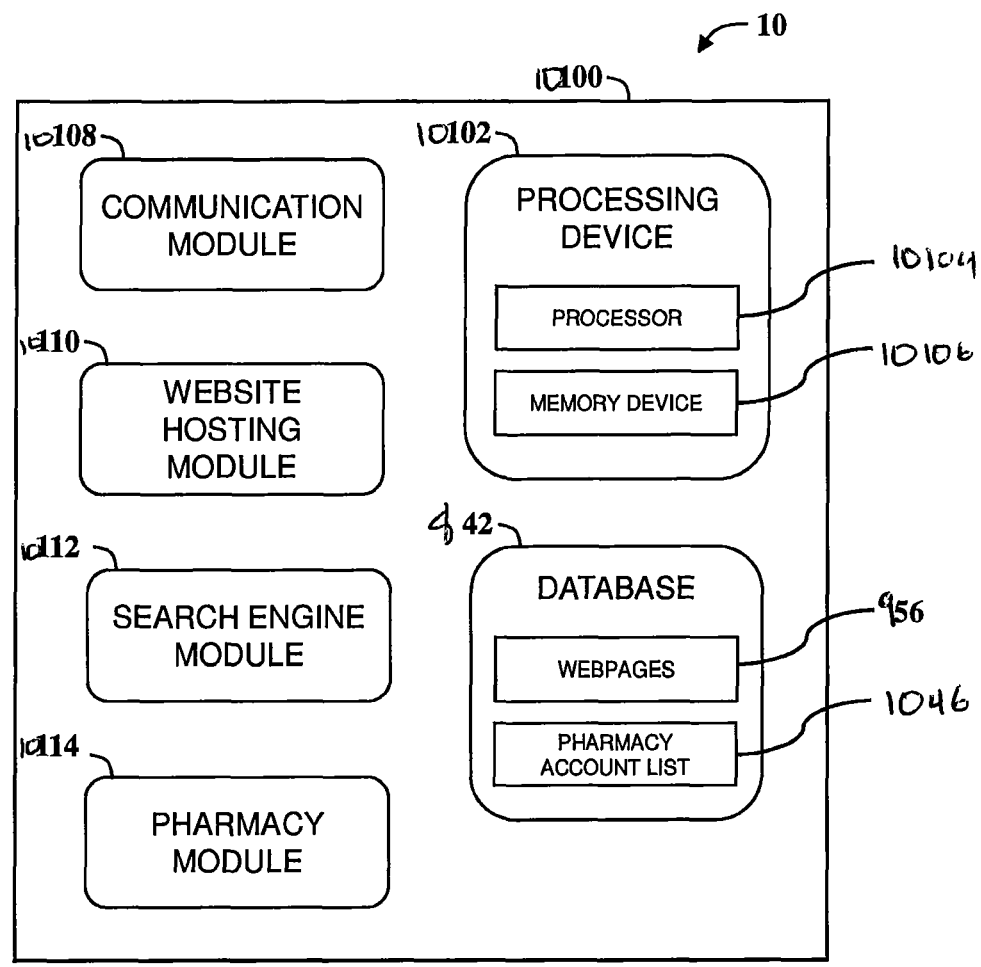
FIG. 10 is a schematic illustrating example components of a server computer that may be used with the system shown in FIG. 8, according to an embodiment of the present invention.

Referring now to FIG. 10, in one embodiment, the system 10 may include a system server 10100 that is configured to perform the functions of the website hosting server 834, the pharmacy account server 836, the search engine server 838, and the database server 840. In the illustrated embodiment, the system server 10100 includes a processing device 10102 and the database 842.

The processing device 10102 executes various programs, and thereby controls components of the system server 10100 according to user instructions received from the user computing device 814. The processing device 10102 may include memory device 10106, e.g., read only memory (ROM) and random access memory (RAM), storing processor-executable instructions and one or more processors that execute the processor-executable instructions. The memory device 10106 may include, but is not limited to, a hard disc drive, an optical disc drive, and/or a flash memory drive. Further, the memory device 10106 may be distributed and located at multiple locations.

In embodiments where the processing device 10102 includes two or more processors 10104, the processors can operate in a parallel or distributed manner. In an example, the processing device 10104 may execute a communications module 10108, a website hosting module 10110, a search engine module 10112, and a pharmacy account module 10114.

The communications module 10108 retrieves various data and information from the database 842 and sends information to the user computing device 814 via the communications network 818 to enable the user to access and interact with the system 10. In one embodiment, the communications module 10108 displays various images on a graphical interface of the user computing device 814 preferably by using computer graphics and image data stored in the database 842 including, but not limited to, web pages, pharmacy records, pharmacy notification messages, product lists, and/or any suitable information and/or images that enable the system 10 to function as described herein.

The website hosting module 10110 may be programmed to perform some or all of the functions of the website hosting server 834 including hosting various web pages associated with one or more websites that are stored in the database 842 and that are accessible to the user via the user computing device 814. The website hosting module 10110 may be programmed to generate and display web pages associated with a website in response to requests being received from users via corresponding web browsers.

The search engine module 10112 may be programmed to perform some or all of the functions of the search engine server 838 including generating and storing search data in response to the user's search request and/or pharmacy account module 10114 search requests.

The pharmacy account module 10114 may be programmed to perform some or all of the functions of the pharmacy account server 836 including monitoring activities associated with pharmacy customers including new prescription and/or prescription refill requests and generate notification messages associated with the monitored activities. In addition, the pharmacy account module 10114 may be programmed to perform calendared tasks requested by the user.

Referring now to FIG. 11, in one embodiment, the database 842 may contain a pharmacy account list 1046 that includes a plurality of user pharmacy account records 1148. Each user pharmacy account record 1148 is associated with a corresponding pharmacy customer and includes user identification information 1150 associated with the pharmacy customer and pharmaceutical drug information 1152 associated with pharmaceutical drugs prescribed to and/or purchased by the corresponding pharmacy customer. The user identification information 1150 includes user identifying data such as, for example, a unique ID and/or password. The user identification information 1150 may also include user contact information such as, for example, a phone number, an email, and/or a mobile device data associated with a mobile computing device 820 associated with the corresponding pharmacy customer. For example, the mobile device data may include, but is not limited to, a unique mobile device ID, operating system, phone number, IP address, mobile device API, and/or any suitable information that enables the system 10 to communicate with the corresponding mobile computing device 820. The pharmaceutical drug information 1152 includes information associated with a corresponding pharmaceutical drug such as, for example, a unique drug ID associated with the pharmaceutical drug, a drug name, drug category, proscribed use information, dosage, number of refills, side effects, and/or any relevant information associated with the corresponding pharmaceutical drug.

Figure 12:
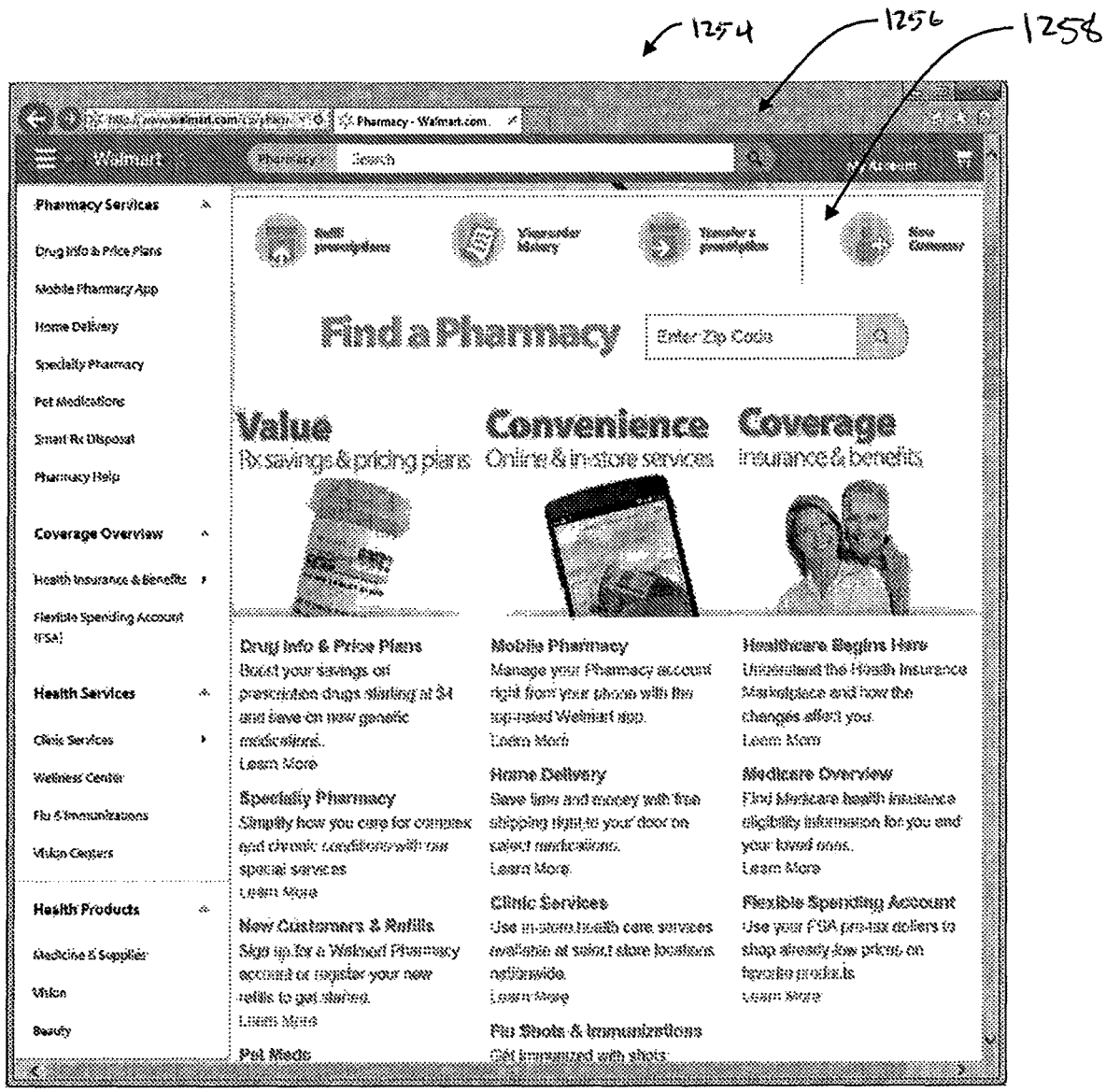
FIGS. 12-17 are illustrations of exemplary screenshots from the system of FIG. 8, according to an embodiment of the present invention.

Referring now to FIG. 12, the website hosting server 834 is configured to host a website 1254 that is accessible by a user via one or more user computing devices 814. The website hosting server 834 retrieves and stores web pages 56 associated with one or more websites 1254 in response to requests received by the user via the user computing device 14 to allow users to interact with the website and search and/or purchase products such as, for example, goods and/or services via the website. In one embodiment, the website hosting server 834 is configured to generate and display web pages 56 associated with the website in response to requests being received from consumers via corresponding web browsers that are displayed on the user computing devices 814.

Figure 13A:
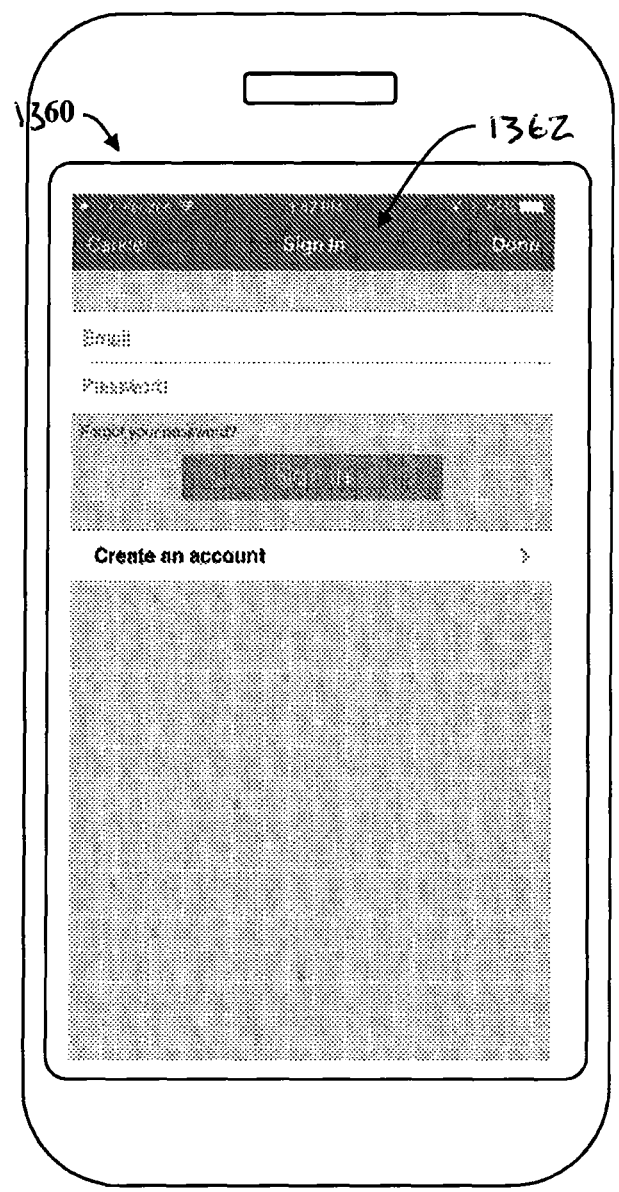
Figure 13B:
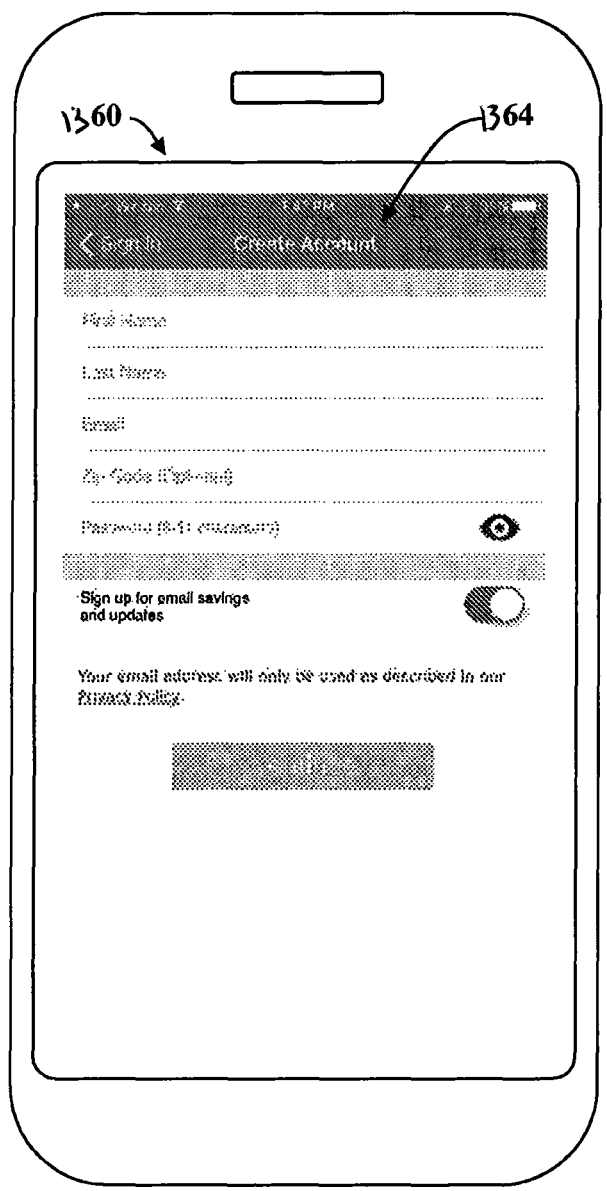

Referring now to FIGS. 13A and 13B, the website hosting server 834 may be configured to generate and display a mobile webpage 1360 that is displayed on one or more mobile computing devices 820. For example, in one embodiment, the website hosting server 834 may display a mobile webpage 1360 in response to receiving a user request that allows a user to access a corresponding customer pharmacy account record 1148. In one embodiment, the website hosting server 834 may allow customers to login and access corresponding customer pharmacy accounts including account information such as, for example, previous purchases, pending prescription orders, pending prescription refills, and/or pharmaceutical drug information. For example, the website hosting server 834 may display a login page 1362 for returning customers or create account page 1364 for new customers, receive a unique customer ID such as, for example, a username and/or password, and identify the customer account associated with the unique customer ID to enable the identified customer to access information and/or features associated with the corresponding customer pharmacy account.

Referring again to FIG. 8, the pharmacy account server 836 is programmed to monitor activities associated with prescription drugs being used by pharmacy customers. In addition, the pharmacy account server 836 is programmed to detect the occurrence of triggering events associated with pharmaceutical drugs being used by pharmacy customers and transmit pharmacy notification messages to the customers to assist the customers with medication adherence.

In one embodiment, the pharmacy account server 836 may determine the triggering event to include an indication of a new prescription or a refilled prescription through the mobile webpage 1360. The pharmacy account server 836 may be programmed to receive a signal indicating a new or updated pharmaceutical drug associated with a pharmacy customer. The signal may include an indication of a new prescription and/or include a request to fill a prescription received from the mobile webpage 1360. In addition, the signal may include a pharmaceutical drug ID and a user ID. In one embodiment, the pharmacy account server 836 may access the pharmacy account list 1046 being stored in the database an determine the user pharmacy account records 1148 that is associated with the received user ID, determine one or more pharmaceutical drugs associated with the user ID, and determine the pharmaceutical drug ID associated with each corresponding pharmaceutical drug.

Figure 14:
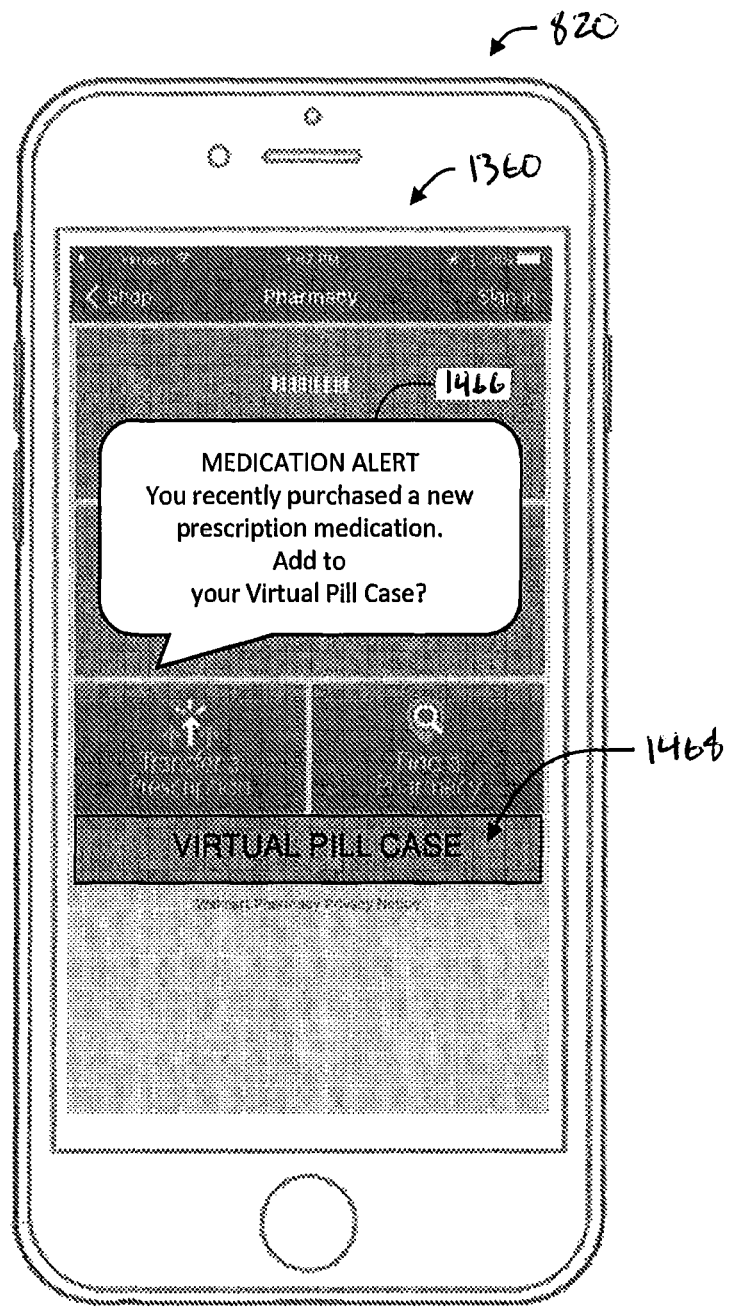

The pharmacy account server 836 may be alerted of the new prescription or new refill by a point-of-sale transaction associated with the user ID. Referring now to FIG. 14, the pharmacy account server 836 generates a pharmacy notification message 1466 requesting that the pharmacy customer add the new prescription or new refill information to the pharmacy customer's virtual pill case 1468. The pharmacy account server 836 then generates and transmits a signal including the pharmacy notification message to the mobile computing device 820 to cause the mobile computing device 820 to display the pharmacy notification message on the mobile computing device 820.

Figure 15:
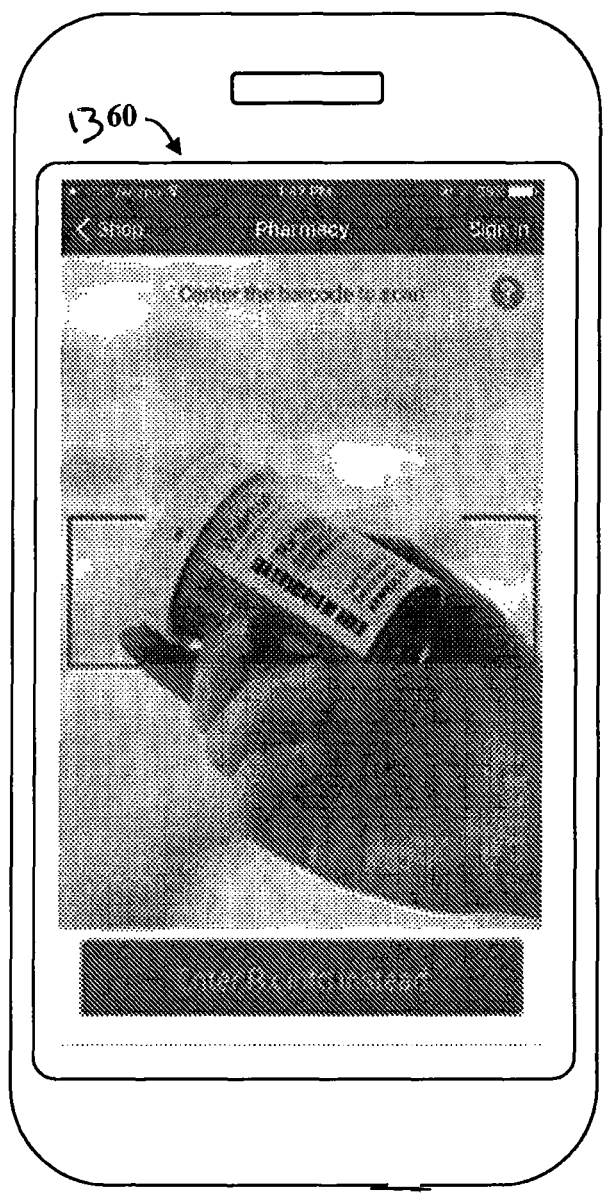

Referring now to FIG. 15, alternatively, the pharmacy customer may indicate the new prescription or new refill to the pharmacy account server 836, which may prompt the user to input the prescription information (e.g., by scanning a barcode associated with the prescription or by manually entering prescription information) via mobile webpage 1360.

In one embodiment, the system 10 may periodically prompt the pharmacy customer to transfer any prescriptions that may be administered by other pharmacies to the pharmacy associated with the virtual pill case.

In one embodiment, once the new prescription or new refill information has been received by the pharmacy account server 836, the pharmacy account server 836 may initiate a data search operation including transmitting the prescription information to the search engine server 838. In one embodiment, during the data search operation, the pharmacy account server 836 generates search terms associated with a prescribed pharmaceutical drug included in the identified user pharmacy account record 1148 and transmits the search terms to the search engine server 838. The search engine server 838 may initiate a search on the third party computer server 816. The search results may be transmitted from the search engine server 838 to the pharmacy account server 836. The search results may include information about the pharmaceutical drug, including information about the pill shape, size, color, and strength, and an image or photograph representing the pill (or inhaler, pump, patch, or other device by which the pharmaceutical drug is administered).

The pharmacy account server 836 may receive the search results from the search engine module 838 and evaluate the search results to retrieve new or updated information associated with the pharmaceutical drug.

Figure 16A:
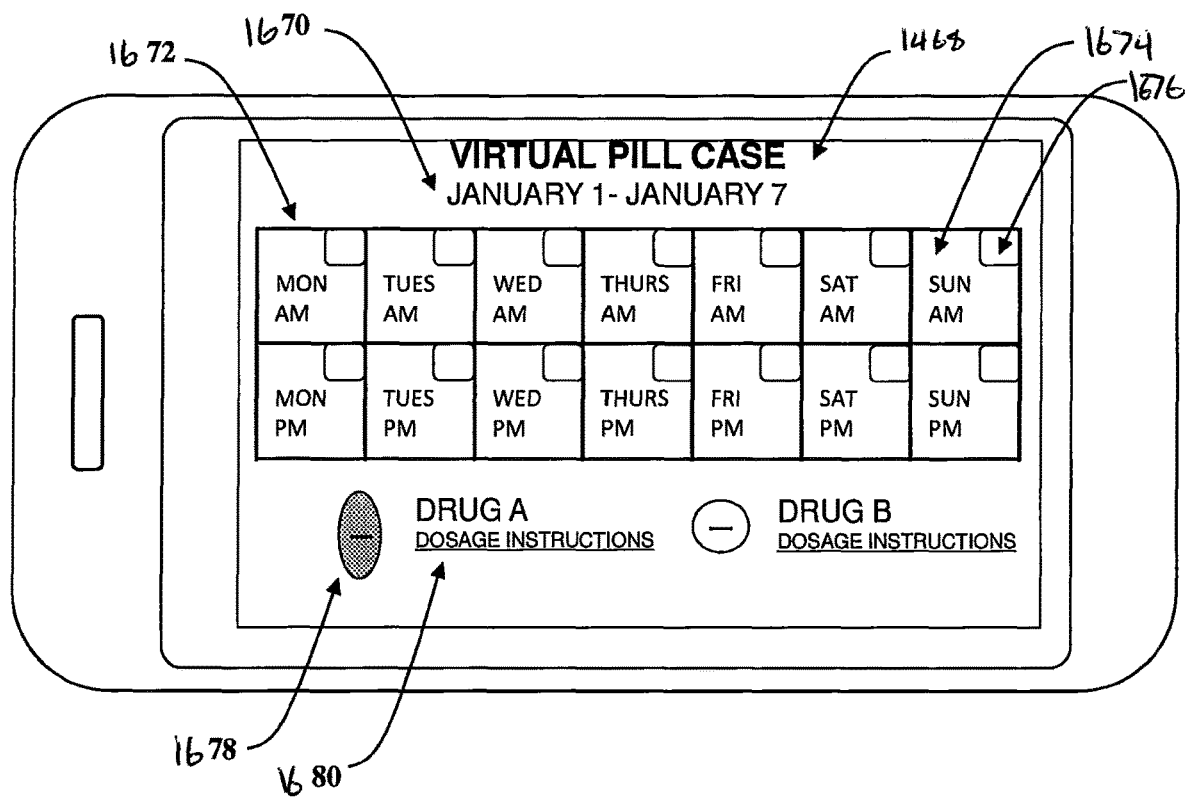

Referring now to FIG. 16A, the pharmacy account server 836 may store the retrieved information about the prescribed pharmaceutical drug and the prescription information in a virtual pill case 1468 associated with the pharmacy customer. The virtual pill case 1468 may display a date range 1670. The date range 1670 may correspond to a calendar 1672, which may have a separate entry 1674 for each day of the week and, in some cases, entries for different times of day (e.g., AM and PM), similar to a traditional physical pill case. Each entry 1674 may have a checkbox 1676 to indicate whether the pharmacy customer has taken the prescribed dose for that day and/or time. An image 1678 showing the pill associated with the pharmaceutical drug may also be displayed, along with a hyperlink 1680 to additional information about the pharmaceutical drug including dosage instructions. All currently prescribed pharmaceutical drugs stored in database 842 and associated with the customer ID of the pharmacy customer will be shown in the virtual pill case 1468 (e.g., DRUG A and DRUG B).

Figure 16B:
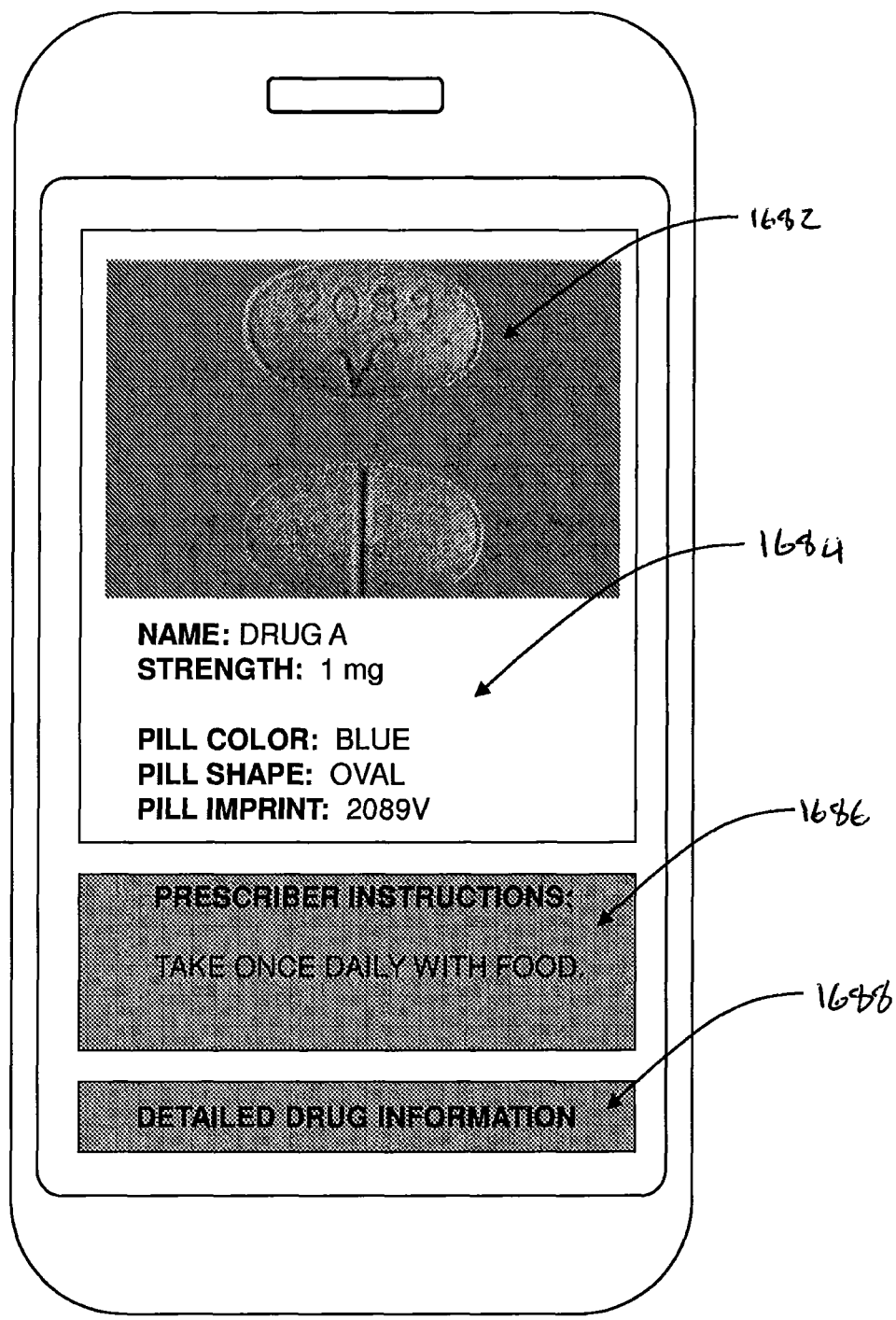

Referring now to FIG. 16B, when the pharmacy customer follows hyperlink 1680 from FIG. 14, the additional information about the pharmaceutical drug is displayed. In the illustrated embodiment, a photograph 1682 shows the pill (or other medication administration device) associated with the pharmaceutical drug. Drug details 1684 include, for example, the name, class, and strength of the drug, as well as the shape, color, and imprint of the pill. Additionally, dosage instructions 1686 are displayed, which include personalized instructions for administration of the medication as prescribed for the pharmacy customer. The pharmacy customer may access additional information via a hyperlink 1688, which may take the pharmacy customer to a third party website and display, for instance, information about side effects and drug and food interactions associated with the pharmaceutical drug.

Figure 16C:
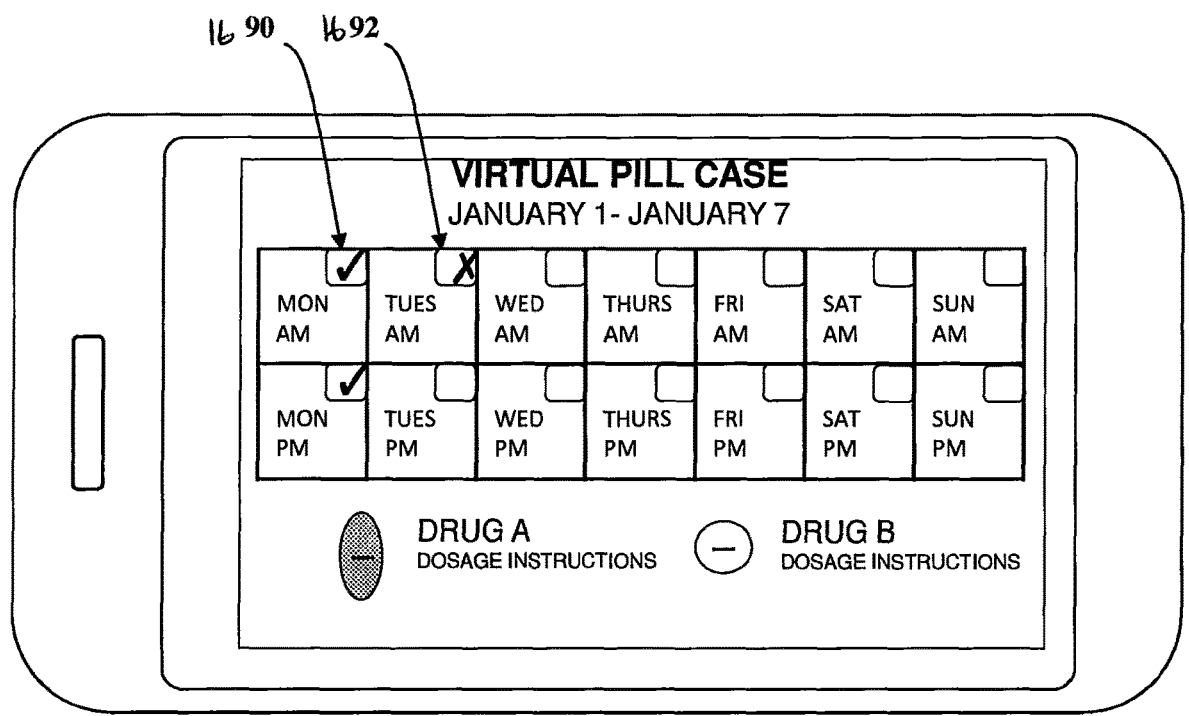

Referring now to FIG. 16C, the pharmacy customer may indicate that a dosage was taken by placing a taken dose symbol 1690. If the pharmacy customer misses a dose, a missed dose symbol 1692 may be shown. In response to a missed dose, a pharmacy notification may be sent to the pharmacy customer.

Figure 17:
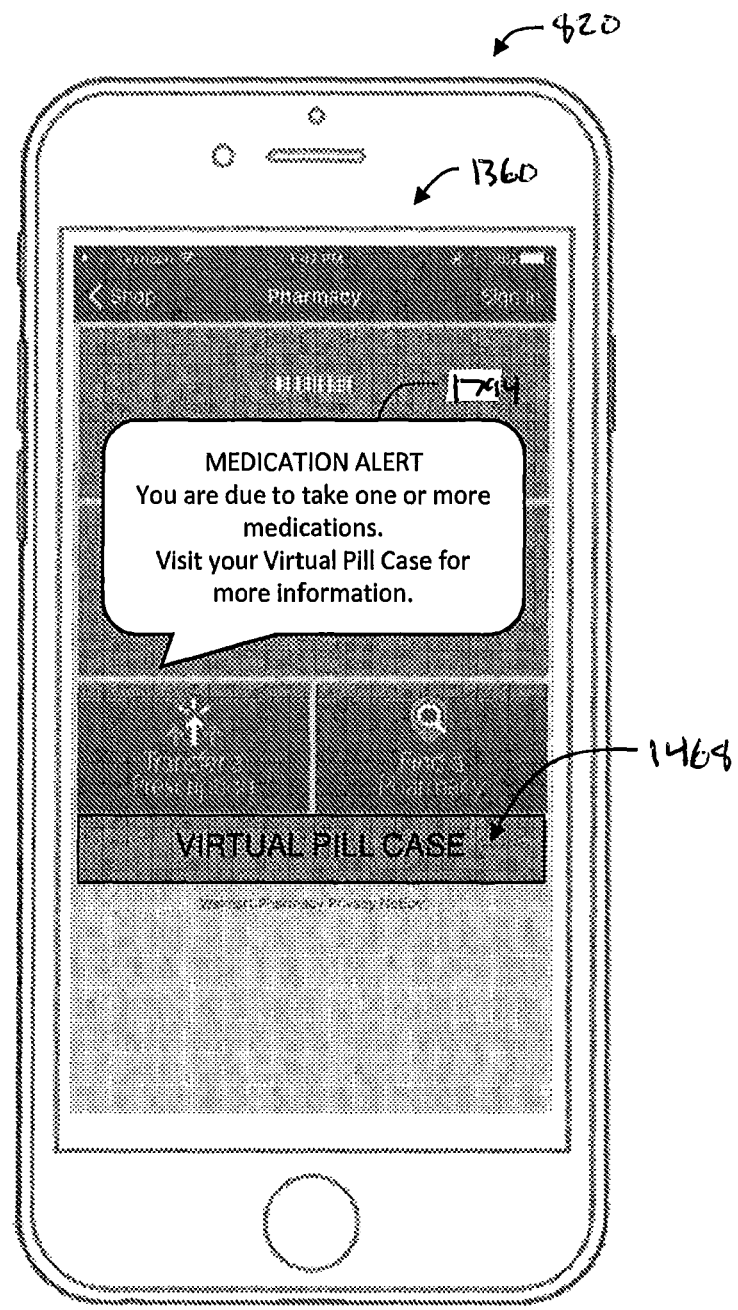

Referring now to FIG. 17, in one embodiment, the pharmacy account server 836 may receive a request to display a pharmacy notification message 1794 to the pharmacy customer via a user computing device 814. In one embodiment, the pharmacy account server 836 may receive a request to display the pharmacy notification message on a mobile computing device 820. The request may include a corresponding user ID. Upon receiving the request, the pharmacy account server 836 accesses the database 842 and identifies a user pharmacy account record 1148 associated with the received user ID. The pharmacy account server 836 detects an occurrence of a triggering event as a function of the triggering event data, such as a missed dose by the pharmacy customer, and generates the pharmacy notification message 1794. The pharmacy account server 836 then generates and transmits a signal including the pharmacy notification message to the mobile computing device 820 to cause the mobile computing device 820 to display the pharmacy notification message on the mobile computing device 820.

FIGS. 18-21 are flowcharts of methods 18200, 19300, 20400, and 21500 that may be used with the system 10 for monitoring activities of pharmacy customers and generating and displaying information to the pharmacy customers on a website via a mobile computing device. The methods include a plurality of steps. Each method step may be performed independently of, or in combination with, other method steps. Portions of the methods may be performed by any one of, or any combination of, the components of the system 10.

Figure 18:
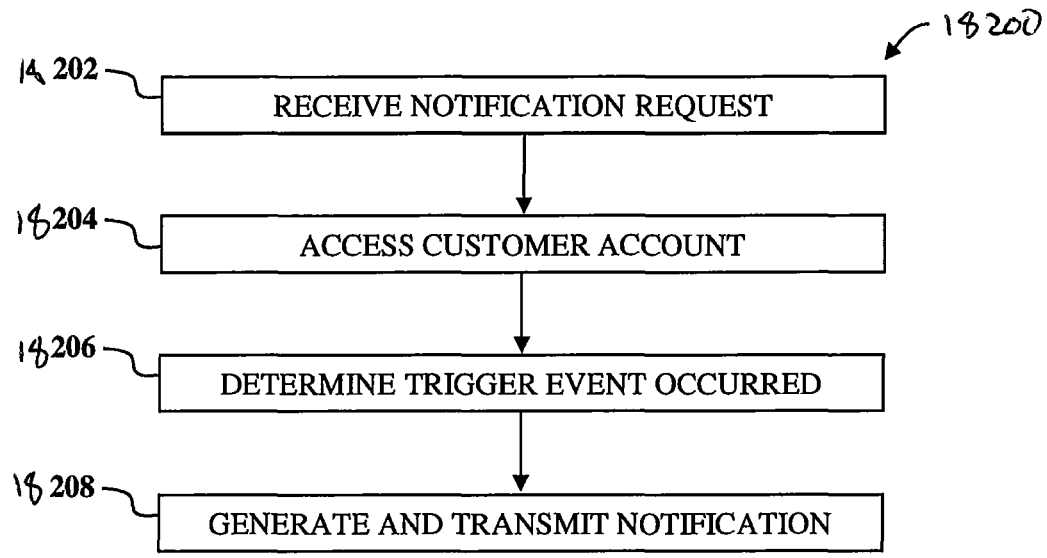
FIGS. 18-21 are flowcharts of methods that may be used with the system shown in FIG. 8, according to embodiments of the present invention.

Referring now to FIG. 18, a method 18200 for determining new prescription information is available is shown. At step 18202, the pharmacy account server 836 receives a request to initiate a notification operation to monitor an activity of a pharmacy customer. The request includes a corresponding user ID. In one embodiment, the request may be received from a mobile computing device 820 associated with a pharmacy customer. In another embodiment, the request may be initiated by the customer via the pharmacy website. In addition, the pharmacy account server 836 may be programmed to initiate a notification operation at a specific time and/or upon receiving an indication of activities associated with a pharmacy customer.

At step 18204, the pharmacy account server 836 accesses the user pharmacy account list 1046 being stored in the database 842 to determine a user pharmacy account records 1148 associated with the received user ID.

At step 18206, the pharmacy account server 836 determines that a triggering event has occurred. For example, in one embodiment, the triggering event may include a purchase of a new prescription by the pharmacy customer associated with the user ID. In another embodiment, the triggering event may include an indication that a pharmaceutical drug associated with the user ID requires a refill.

At step 18208, the pharmacy account server 836 generates and transmits a pharmacy notification message to the pharmacy customer requesting that the pharmacy customer add the new prescription information to the pharmacy customer's virtual pill case 1468. In the illustrated embodiment, the pharmacy account server 836 generates and transmits a signal including the notification message to the mobile computing device 820 to cause the mobile computing device 820 to display the notification message on the mobile computing device 820. For example, the pharmacy account server 836 may generate a notification 1466 (shown in FIG. 14) upon detecting a new prescription or new refill. In one embodiment, the system 10 may access the corresponding user pharmacy account records 1148 to determine a messaging API associated with an operating system of the mobile computing device 820 and generate the notification message as a function of the retrieved messaging API to enable the mobile computing device 820 to display the received message. In one embodiment, each user account record includes information associated with the mobile computing device 820 including a unique mobile ID and message API. In another embodiment, the user pharmacy account records 1148 may include a message preferences, such as, for example, an email, text message, push messaging, automated phone call, and the like. The pharmacy account server 836 identifies the messaging preference associated with the user pharmacy account records 1148 and generates the notification message based on the message preference.

Figure 19:
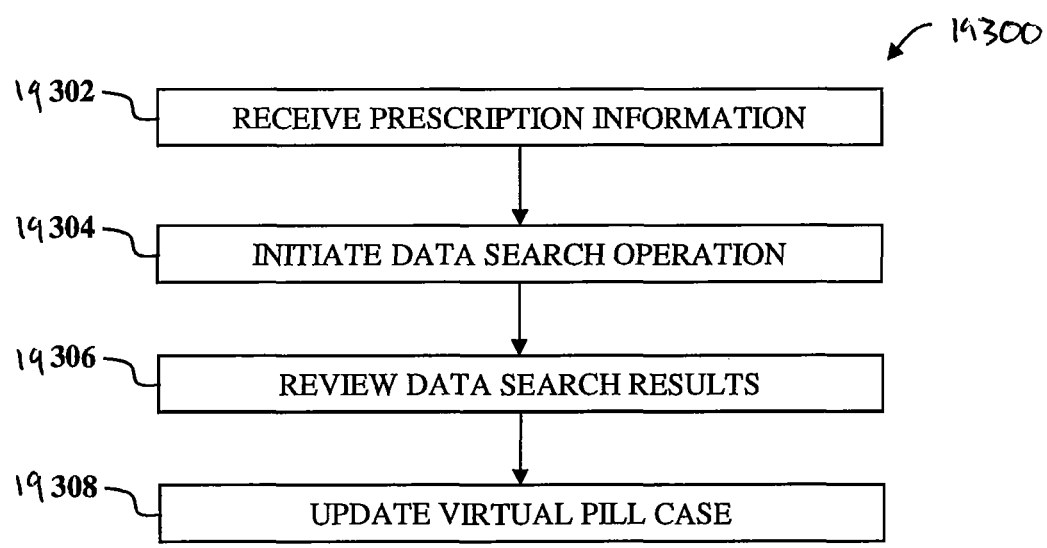

Referring now to FIG. 19, a method 19300 for acquiring new prescription information is shown. At step 19302, prescription information is received (e.g., manually entered by the pharmacy customer or received via an electronic transaction record).

At step 19304, the pharmacy account server 836 initiates a data search operation including transmitting the prescription information to the search engine server 838. In one embodiment, during the data search operation, the pharmacy account server 836 generates search terms associated with a prescribed pharmaceutical drug included in the identified user pharmacy account record 1148 and transmits the search terms to the search engine server 838. The search engine server 838 may initiate a search on the third party computer server 816. The search results may be transmitted from the search engine server 838 to the pharmacy account server 836. The search results may include information about the pharmaceutical drug, including information about the pill shape, size, color, and strength, and an image or photograph representing the pill (or inhaler, pump, patch, or other device by which the pharmaceutical drug is administered).

At step 19306, the pharmacy account server 836 reviews the data search results and determines whether new information not already stored in the virtual pill case has been retrieved. For example, the prescription information may correspond to a refill of a pharmaceutical drug that is already stored in the pharmacy customer's virtual pill case, but the search results may indicate new information is available for the pharmaceutical drug because the manufacturer has changed the pill shape since the pharmacy customer's previous refill.

At step 19308, the virtual pill case is updated with any new information retrieved via the search results.

Figure 20:
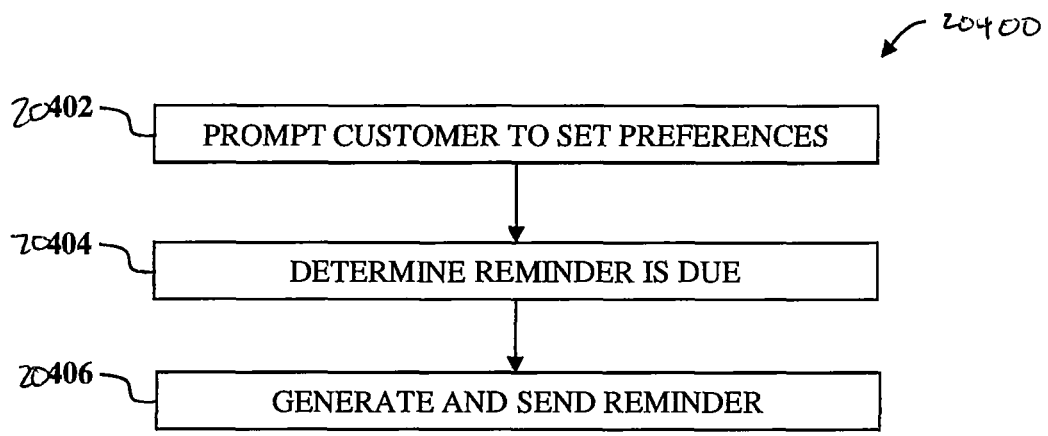

Referring now to FIG. 20, a method 20400 for sending a reminder to pharmacy customer regarding a virtual pill case. At step 20402, the pharmacy account server 836 prompts a pharmacy customer to set one or more reminder preferences regarding a virtual pill case. Reminder preferences may include, for example, whether the customer wishes to receive reminders regarding the virtual pill case. If the customer wishes to receive reminders, the customer may indicate a frequency with which the reminder should be sent (e.g., daily, weekly, etc.) and when the reminder should be sent (e.g., in the morning, afternoon, or evening, or at a specific time). The user may also indicate whether the reminder should be sent only if the user has missed a scheduled medication dose, or if the reminder should always be sent. Additionally, the user may indicate the preferred method of transmission of the reminder (e.g., push notification, text message, e-mail, etc.).

At step 20404, the pharmacy account server 836 determines that a reminder to the pharmacy customer is due, based on the customer's set reminder preferences. At step 20406, the pharmacy account server 836 generates and sends a reminder to the pharmacy customer regarding the virtual pill case.

Figure 21:
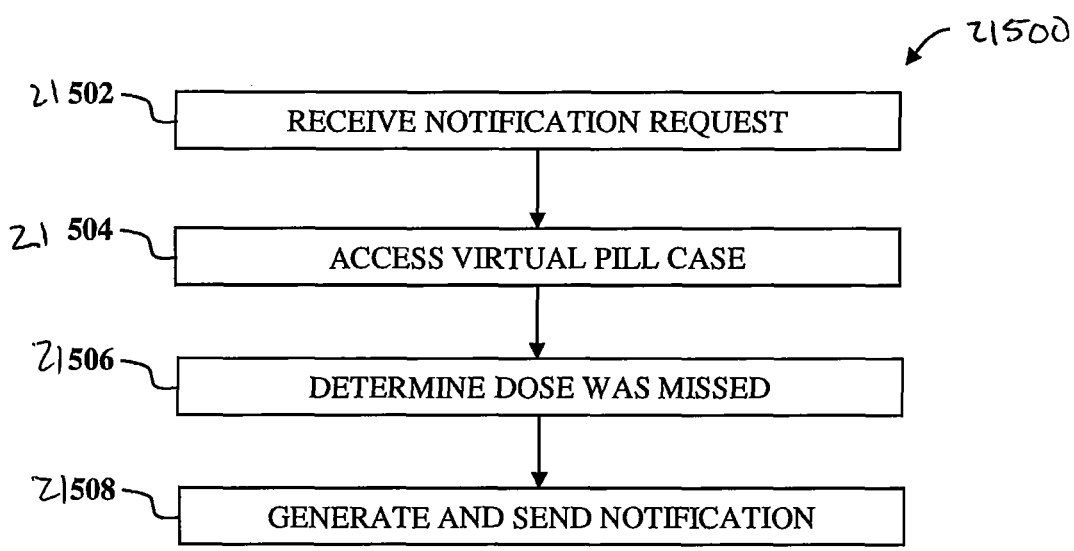

Referring now to FIG. 21, a method 21500 for sending a missed dose notification to pharmacy customer using a virtual pill case. At step 21502, the pharmacy account server 836 receives a request to initiate a notification operation to monitor an activity of a pharmacy customer. The request includes a corresponding user ID. In one embodiment, the request may be received from a mobile computing device 820 associated with a pharmacy customer. In another embodiment, the request may be initiated by the customer via the pharmacy website. In addition, the pharmacy account server 836 may be programmed to initiate a notification operation at a specific time and/or upon receiving an indication of activities associated with a pharmacy customer.

At step 21504, the pharmacy account server 836 accesses a virtual pill case associated with the pharmacy customer. At step 21506, the pharmacy account server 836 determines that the pharmacy customer missed at least one scheduled dose of a pharmaceutical drug according to dosage instructions provided by a prescriber. At step 21508, the pharmacy account server 836 generates and sends a notification to the pharmacy customer regarding the missed dose and prompting the user to visit the virtual pill case to review dosage instructions.

The present invention has been described in an illustrative manner. It is to be understood that the terminology, which has been used, is intended to be in the nature of words of description rather than of limitation.

Many modifications and variations of the present invention are possible in light of the above teachings. Therefore, within the scope of the appended claims, the present invention may be practiced other than as specifically described.

What is claimed is:

1. A method comprising:
   receiving, by a computer system, a GPS location of a user;
   querying, by the computer system, a store location database comprising retail store locations for retail stores of a retailer;
   determining, by the computing system, one or more store locations of the retail store locations near the GPS location of the user;
   receiving, by the computer system, a selected product to be located in at least one retail store of the retailer inputted by the user into a mobile computer application running on a mobile computing device, the at least one retail store of the retailer located at a store location of the one or more store locations;
   performing a search, by the computer system, for the selected product on product records corresponding to a plurality of products offered by the retailer at the at least one retail store of the retailer;
   identifying, in response to the search and by the computer system, one or more of the product records relevant to the selected product;
   transmitting, by the computer system, the one or more of the product records for at least one product identified as one or more search results for the search;
   when the selected product is out of stock at the at least one retail store, transmitting, by the computer system, additional locations of the one or more store locations, the additional locations having the selected product in stock;
   when the selected product is a pharmacy product:
      facilitating a display, by the computer system onto the mobile computing device, of a first user interface displaying a virtual pill case comprising:
         a date range;
         first prescription information about at least one medication, wherein:
            the first prescription information comprises dosage instructions for the at least one medication; and
            the at least one medication is scheduled to be taken by the user during the date range;
         a selectable user interface element corresponding to the at least one medication;
         a first pictorial representation of the at least one medication; and
         a customized hyperlink;
      receiving, from the user, a first selection of the selectable user interface element corresponding to the at least one medication, the first selection indicating a use of the at least one medication by the user;
      transmitting the first selection to a computer server for storage;
      receiving, from the user, a second selection of the customized hyperlink; and
      in response to receiving the second selection of the customized hyperlink, facilitating a display, on the mobile computing device, of a second user interface comprising:
         a digital photograph of the at least one medication; and
         second prescription information about the at least one medication, the second prescription information comprising:
            a name of a pharmaceutical drug;
            a class of the pharmaceutical drug;
            a dosage strength of the pharmaceutical drug;
            a shape of the pharmaceutical drug;
            a color of the pharmaceutical drug; and
            an imprint of the pharmaceutical drug;
   suggesting, by the computer system, at least one related product to the selected product;
   adding the at least one related product to the one or more search results;
   facilitating a display, by the computer system onto the mobile computing device, of the one or more search results and the additional locations to the mobile computer application running on the mobile computing device, wherein the one or more search results are associated with products of the plurality of products offered by the retailer; and
   receiving, by the computer system, at least one of the at least one product or at least one of the at least one related product from the one or more search results selected by the user using the mobile computer application running on the mobile computing device to be shipped to an address of the at least one retail store or another address received from the user.

2. The method as set forth in claim 1 further comprising receiving a scan of a shelf-tag for the selected product or a search query for the selected product inputted into the mobile computing device.

3. The method as set forth in claim 2 further comprising storing the product records in a product database.

4. The method as set forth in claim 3 further comprising searching the selected product within the product database of the retailer using the mobile computer application running on the mobile computing device.

5. The method as set forth in claim 2 further comprising outputting products offered by the retailer as a list of the one or more search results based on the search query.

6. The method as set forth in claim 2 further comprising receiving a name of the selected product as part of the search query.

7. The method as set forth in claim 1 further comprising receiving an order for the at least one product or the at least one related product to be shipped to the user.

8. The method as set forth in claim 7 further comprising receiving the another address from the mobile computer application running on the mobile computing device.

9. The method as set forth in claim 1 further comprising receiving payment from the user for the at least one of the at least one product or the at least one of the at least one related product from a sales system of the at least one retail store or on-line from the mobile computer application running on the mobile computing device.

10. One or more non-transitory computer-readable storage media, having computer-executable instructions embodied thereon, wherein when executed by at least one processor, the computer-executable instructions cause the processor to:
- receive a GPS location of a user;
- query a store location database comprising retail store locations for retail stores of a retailer;
- determine one or more store locations of the retail store locations near the GPS location of the user;
- receive a selected product to be located in at least one retail store of the retailer inputted by the user into a mobile computer application running on a mobile computing device, the at least one retail store of the retailer located at a store location of the one or more store locations;
- perform a search for the selected product on product records corresponding to a plurality of products offered by the retailer at the at least one retail store of the retailer;
- identify, in response to the search, one or more of the product records relevant to the selected product;
- transmit the one or more of the product records identified for at least one product as one or more search results for the search;
- when the selected product is out of stock at the at least one retail store, transmit additional locations of the one or more store locations, the additional locations having the selected product in stock;
- when the selected product is a pharmacy product:
  - facilitate a display, by a computer system onto the mobile computing device, of a first user interface displaying a virtual pill case comprising:
    - a date range;
    - first prescription information about at least one medication, wherein:
      - the first prescription information comprises dosage instructions for the at least one medication; and
      - the at least one medication is scheduled to be taken by the user during the date range;
    - a selectable user interface element corresponding to the at least one medication;
    - a first pictorial representation of the at least one medication; and
    - a customized hyperlink;
  - receive, from the user, a first selection of the selectable user interface element corresponding to the at least one medication, the first selection indicating a use of the at least one medication by the user;
  - transmit the first selection to a computer server for storage;
  - receive, from the user, a second selection of the customized hyperlink; and
  - in response to receiving the second selection of the customized hyperlink, facilitate a display, on the mobile computing device, of a second user interface comprising:
    - a digital photograph of the at least one medication; and
    - second prescription information about the at least one medication, the second prescription information comprising:
      - a name of a pharmaceutical drug;
      - a class of the pharmaceutical drug;
      - a dosage strength of the pharmaceutical drug;
      - a shape of the pharmaceutical drug;
      - a color of the pharmaceutical drug; and
      - an imprint of the pharmaceutical drug;
- suggest at least one related product to the selected product;
- add the at least one related product to the one or more search results;
- facilitate a display, on the mobile computing device, of the one or more search results and the additional locations to the mobile computer application running on the mobile computing device, each of the one or more search results being associated with a product offered by the retailer;
- receive at least one of the at least one product or at least one of the at least one related product from the one or more search results selected by the user using the mobile computer application running on the mobile computing device to be shipped to an address of the at least one retail store or another address received from the user.

11. A system comprising:
one or more processing modules; and
one or more non-transitory storage modules storing computing instructions configured to run on the one or more processing modules and perform acts of:
- receiving a GPS location of a user;
- querying a store location database comprising retail store locations for retail stores of a retailer;
- determining one or more store locations of the retail store locations near the GPS location of the user;
- receiving a selected product to be located in at least one retail store of the retailer inputted by the user into a mobile computer application running on a mobile computing device, the at least one retail store of the retailer located at a store location of the one or more store locations;
- performing a search for the selected product on product records corresponding to a plurality of products offered by the retailer at the at least one retail store of the retailer;
- identifying, in response to the search, one or more of the product records relevant to the selected product;
- transmitting, by a computer system, the one or more of the product records for at least one product identified as one or more search results for the search;
- when the selected product is out of stock at the at least one retail store, transmitting additional locations of the one or more store locations, the additional locations having the selected product in stock;
- when the selected product is a pharmacy product:
  - facilitating a display, by the computer system onto the mobile computing device, of a first user interface displaying a virtual pill case comprising:

a date range;
first prescription information about at least one medication,
wherein:
the first prescription information comprises dosage instructions for the at least one medication; and
the at least one medication is scheduled to be taken by the user during the date range;
a selectable user interface element corresponding to the at least one medication;
a first pictorial representation of the at least one medication; and
a customized hyperlink;
receiving, from the user, a first selection of the selectable user interface element corresponding to the at least one medication, the first selection indicating a use of the at least one medication by the user;
transmitting the first selection to a computer server for storage;
receiving, from the user, a second selection of the customized hyperlink; and
in response to receiving the second selection of the customized hyperlink, facilitating a display, on the mobile computing device, of a second user interface comprising:
a digital photograph of the at least one medication; and
second prescription information about the at least one medication, the second prescription information comprising:
a name of a pharmaceutical drug;
a class of the pharmaceutical drug;
a dosage strength of the pharmaceutical drug;
a shape of the pharmaceutical drug;
a color of the pharmaceutical drug; and
an imprint of the pharmaceutical drug;
providing the one or more search results and the additional locations to the mobile computer application running on the mobile computing device, each of the one or more search results being associated with a product offered by the retailer;
suggesting at least one related product to the selected product;
adding the at least one related product to the one or more search results; and
receiving at least one of the at least one product or at least one of the at least one related product from the one or more search results selected by the user using the mobile computer application running on the mobile computing device to be shipped to an address of the at least one retail store or another address received from the user.

12. The system of claim 11, wherein the computing instructions are further configured to perform an act of:
receiving a scan of a shelf-tag for the selected product or a search query for the selected product inputted into the mobile computing device.

13. The system of claim 12, wherein the computing instructions are further configured to perform an act of:
storing the product records in a product database.

14. The system of claim 13, wherein the computing instructions are further configured to perform an act of:
searching the selected product within the product database of the retailer using the mobile computer application running on the mobile computing device.

15. The system of claim 12, wherein the computing instructions are further configured to perform an act of:
outputting products offered by the retailer as a list of the one or more search results based on the search query.

16. The system of claim 12, wherein the computing instructions are further configured to perform an act of:
receiving a name of the selected product as part of the search query.

17. The system of claim 11, wherein the computing instructions are further configured to perform an act of:
receiving an order for the at least one product or the at least one related product to be shipped to the user.

18. The system of claim 17, wherein the computing instructions are further configured to perform an act of:
receiving the another address from the mobile computer application running on the mobile computing device.

19. The system of claim 11, wherein the computing instructions are further configured to perform an act of:
receiving payment from the user for the at least one of the at least one product or the at least one of the at least one related product from a sales system of the at least one retail store or on-line from the mobile computer application running on the mobile computing device.

20. The one or more non-transitory computer-readable storage media of claim 10, wherein the computer-executable instructions further cause the processor to:
receive a scan of a shelf-tag for the selected product or a search query for the selected product inputted into the mobile computing device.

* * * * *